(12) United States Patent
Chen et al.

(10) Patent No.: US 8,546,125 B2
(45) Date of Patent: Oct. 1, 2013

(54) RECOMBINANT HOSTS AND METHODS FOR MANUFACTURING POLYHYDROXYALKANOATE

(75) Inventors: Guo-Qiang Chen, Beijing (CN); Zheng-Jun Li, Beijing (CN); Zhen-Yu Shi, Mordialloc (AU); Ying-Ying Guo, Beijing (CN); Jia Jian, Beijing (CN); Qiong Wu, Beijing (CN)

(73) Assignee: Tianjin Greenbio Material Co., Ltd., Tianjin (CN)

( * ) Notice: Subject to any disclaimer, the term of this patent is extended or adjusted under 35 U.S.C. 154(b) by 0 days.

(21) Appl. No.: 13/031,350

(22) Filed: Feb. 21, 2011

(65) Prior Publication Data

US 2012/0214213 A1    Aug. 23, 2012

(51) Int. Cl.
*C12N 1/20* (2006.01)
*C12P 9/00* (2006.01)
*C07H 21/04* (2006.01)

(52) U.S. Cl.
USPC .................. 435/252.33; 435/135; 536/24.33; 536/23.4

(58) Field of Classification Search
None
See application file for complete search history.

(56) References Cited

U.S. PATENT DOCUMENTS 6,117,658 A    9/2000    Dennis et al.

OTHER PUBLICATIONS

Whisstock et al. Qut Rev of Biophy. 2003, 36, pp. 307-340.*

* cited by examiner

*Primary Examiner* — Tekchand Saidha
*Assistant Examiner* — Younus Meah
(74) *Attorney, Agent, or Firm* — Fay Sharpe LLP

(57) ABSTRACT

Known attempts using engineered bacteria to produce P(3HB-co-4HB) with carbon sources that are structurally unrelated to 4-hydroxybutyrate resulted in relatively low 4HB monomer content of 1.5 to 5 mol %. The current invention provides recombinant hosts for producing P(3HB-co-4HB) wherein the plasmid including succinate semialdehyde dehydrogenase gene (sucD gene) and 4-hydroxybutyrate dehydrogenase gene (4hbD gene) further includes pyruvate decarboxylase promoter ($P_{pdc}$). It was found that the 4HB monomer content in P(3HB-co-4HB) is significantly enhanced to be over 20 mol %, in the range of 8.8 to 23 mol %.

6 Claims, 3 Drawing Sheets

RECOMBINANT HOSTS AND METHODS FOR MANUFACTURING POLYHYDROXYALKANOATE

FIELD OF THE INVENTION

This invention relates to recombinant hosts and methods for manufacturing polyhydroxyalkanoate, particularly poly (3-hydroxybutyrate-co-4-hydroxybutyrate), more particularly those with high 4-hydroxybutyrate monomer content, even more particularly with those that do not utilize carbon sources that are structurally unrelated to 4-hydroxybutyrate.

BACKGROUND OF THE INVENTION

Polyhydroxyalkanoates (PHA) are polyesters synthesized by a variety of bacterial strains as intracellular carbon and energy storage compounds grown usually under stress conditions. As biodegradable and biocompatible materials, Poly (3-hydroxybutyrate-co-4-hydroxybutyrate) [P(3HB-co-4HB)] was first found from *Ralstonia eutropha* cultivated with 4-hydroxybutyric or 4-chlorobutyric acid as carbon sources in 1988. The incorporation of 4HB units into P(3HB) improves the material application potentials, and the copolymers show a wide range of physical properties ranging from highly crystalline plastic to elastic rubber, depending on the polymer composition. P(3HB-co-4HB) with various 4HB compositions are promising materials that have favorable biodegradability and mechanical properties.

Generally, carbon sources structurally related to 4HB are required to generate 4HB-containing PHA, such as 4-hydroxybutyric acid, γ-butyrolactone and 1,4-. However, these carbon sources are much more expensive than glucose or other 3HB-generating carbon sources. For example, 4-hydroxybutyric acid is considered to be the most effective precursor for forming 4HB monomer, but it is difficult to obtain since 4-hydroxybutyric acid is a controlled substance in countries including USA and China. The high cost of raw material for the copolymer production has become an obstacle for the wide production and application of P(3HB-co-4HB).

There were attempts using engineered bacteria to produce P(3HB-co-4HB) with carbon sources that are structurally unrelated to 4-hydroxybutyrate. U.S. Pat. No. 6,117,658 utilizes the PHA biosynthetic pathway in combination with a succinic semialdehyde metabolic pathway to produce P(3HB-co-4HB) in a recombinant host. The host cell contains a recombinant nucleotide sequence encoding the PHA biosynthetic pathway, and another recombinant nucleotide sequence encoding the succinic semialdehyde metabolic pathway. However, 4HB monomer content in the P(3HB-co-4HB) is relatively low, from 1.5 to 5 mol %, while it is common regarded that P(3HB-co-4HB) may show desirable physical properties when the 4HB content in the polymer is higher than 10 mol %. The full content of U.S. Pat. No. 6,117,658 is incorporated herein as reference to the current specification.

There is a need in the art for constructs and methods of producing P(3HB-co-4HB) with high 4HB monomer content using carbon sources are structurally unrelated to 4-hydroxybutyrate in an efficient and cost-effective manner.

OBJECTS OF THE INVENTION

Therefore, it is an object of this invention to resolve at least one or more of the problems as set forth in the prior art. Particularly, it is an object of the current invention to provide an recombinant host cells capable of producing P(3HB-co-4HB) with high 4HB monomer content using carbon sources are structurally unrelated to 4-hydroxybutyrate in an efficient and cost-effective manner. As a minimum, it is an object of this invention to provide the public with a useful choice.

SUMMARY OF THE INVENTION

Accordingly, this invention provides a recombinant host for manufacturing polyhydroxyalkanoate, wherein
native succinate semialdehyde dehydrogenase gene is removed from said recombinant host; and
a first plasmid and a second plasmid including genes for manufacturing the polyhydroxyalkanoate are transformed to the recombinant host, the first plasmid includes 4-hydroxybutyrate-CoA:CoA transferase gene (orfZ gene), β-ketothiolase gene (phaA gene), NADPH-dependent acetoacetyl-CoA reductase gene (phaB gene), and polyhydroxyalkanoate synthase gene (phaC gene), and the second plasmid includes succinate semialdehyde dehydrogenase gene (sucD gene) and 4-hydroxybutyrate dehydrogenase gene (4hbD gene);
characterized in that the second plasmid further includes pyruvate decarboxylase promoter ($P_{pdc}$).
Preferably, the polyhydroxyalkanoate is a copolymer of 3-hydroxybutyrate and 4-hydroxybutyrate.
Preferably, the host is *Escherichia coli*. More preferably, the native succinate semialdehyde dehydrogenase gene is sad and/or gabD genes. Even more preferably, the native succinate semialdehyde dehydrogenase gene is sad gene, or alternatively, sad and gabD genes.

It is another aspect of this invention to provide a method of manufacturing polyhydroxyalkanoate, including the steps of mixing carbohydrate with a recombinant host as above.
Preferably, the carbohydrate is glucose. More preferably, the method further includes the step of mixing a tricarboxylic acid cycle intermediate with the glucose and the recombinant host. Additionally, the tricarboxylic acid cycle intermediate is selected from the group consisting of α-ketoglutarate, oxaloacetate, citrate, succinate, and their mixtures. Even more preferably, the tricarboxylic acid cycle intermediate is mixed at a concentration of less than 2 gram per liter.

It is yet another aspect of the current invention to provide nucleotide sequence or its complimentary sequence of any one of SEQ ID NO 1 to 17.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENTS

This invention is now described by way of examples with reference to the figures in the following paragraphs. Objects, features, and aspects of the present invention are disclosed in or are apparent from the following description. It is to be understood by one of ordinary skill in the art that the present discussion is a description of exemplary embodiments only, and is not intended as limiting the broader aspects of the present invention, which broader aspects are embodied in the exemplary constructions. List 1 is a list showing the full names of the abbreviations used to represent the enzymes in the figures.

List 1

| Gene encoded enzyme | Enzyme |
|---|---|
| phaA | β-ketothiolase |
| phaB | NADPH-dependent acetoacetyl-CoA reductase |
| phaC | PHA synthase |
| sucD | succinate semialdehyde dehydrogenase |
| 4hbD | 4-hydroxybutyrate dehydrogenase |
| orzf | CoA transferase |
| sad | succinate semialdehyde dehydrogenase of E. coli |
| gabD | succinate semialdehyde dehydrogenase of E. coli |

In the current invention, based on the methods and constructs in U.S. Pat. No. 6,117,658, it was found that the 4HB monomer content in P(3HB-co-4HB) is significantly enhanced when the plasmid including succinate semialdehyde dehydrogenase gene (sucD gene) and 4-hydroxybutyrate dehydrogenase gene (4hbD gene) further includes pyruvate decarboxylase promoter ($P_{pdc}$). The 4HB monomer content in the P(3HB-co-4HB) produced by the current invention can be over 20 mol %, in the range of 8.8 to 23 mol %. This is much higher than that in U.S. Pat. No. 6,117,658.

Although the host cell used in the examples below is *Escherichia coli*, other host cells could also be used, including *Klebsiella aerogenes*, *Klebsiella aerogenes*, and *Klebsiella oxytoca*. Other than *E. coli* JM109 used in the examples below, *E. coli* DH5α, Top10, XL1-Blue, HB101 and so on could also be used for the current invention.

Figure 1:
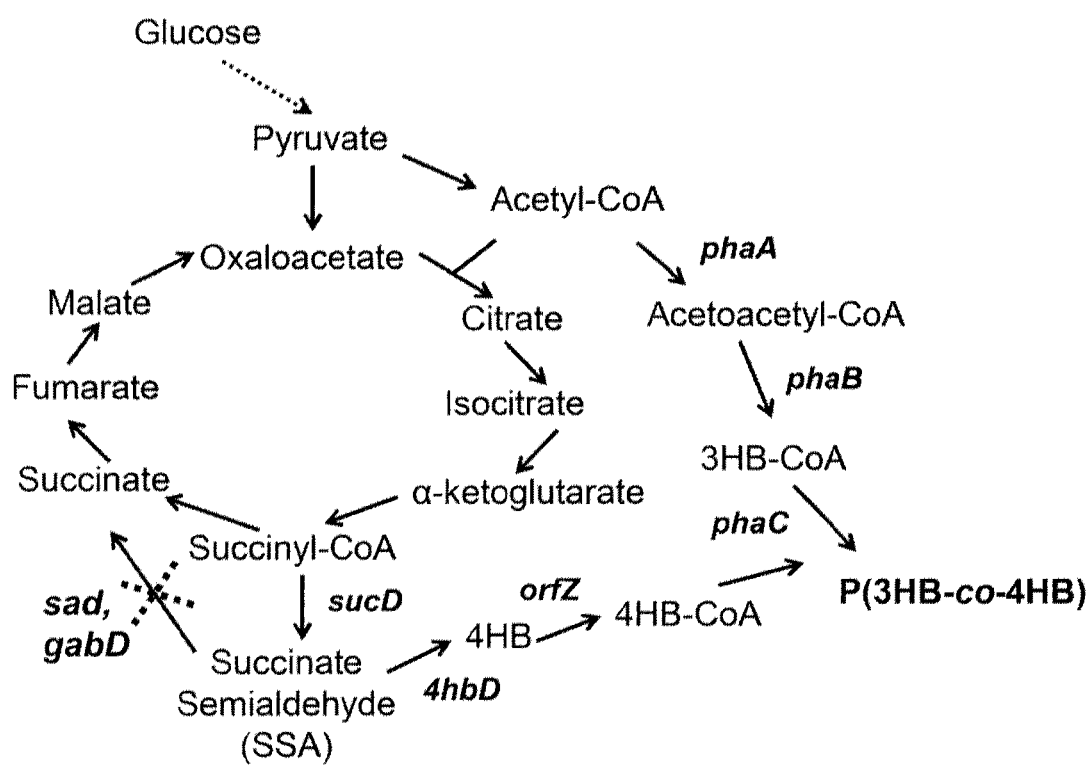
FIG. 1 shows the P(3HB-co-4HB) biosynthesis pathway of the genetically engineered host cell in this invention, in which the host cell in this example is *Escherichia coli.

Various carbon sources that are structurally unrelated to 4-hydroxybutyrate can be used in this invention to produce P(3HB-co-4HB), for example glucose. Additional tricarboxylic acid cycle intermediate, for example α-ketoglutarate, oxaloacetate, citrate, succinate, and their mixtures could also be added. Referring to FIG. 1, these carboxylates are intermediates in the metabolic pathway of producing succinyl-CoA, and their addition could increase the level of succinyl-CoA and thereby increasing the 4HB content in the final P(3HB-co-4HB).

Specific examples using genetically engineered *E. coli* JM109 in producing P(3HB-co-4HB) are described in various sections below.

1. Materials and Methods
1.1. Microorganisms, Plasmids and Medium

The bacterial strains and plasmids used in this invention are listed in Table 1.

TABLE 1

Strains and plasmids used in the examples of this invention

| Strains/plasmids | Description | Reference/source |
|---|---|---|
| E. coli MG1655 | F− λ− rph-1 (wild-type) | Sauer et al., 2004 |
| E. coli JM109 | recA1 endA1 gyrA96 thi-1 hsdR17 supE44 relA1 Δ(lac-proAB)/F′[traD36 proAB+ lacI$^q$ lacZΔM15] | TaKaRa Bio Inc |
| E. coli JM109S | JM109 Δsad | Current invention |
| E. coli JM109G | JM109 ΔgabD | Current invention |
| E. coli JM109SG | JM109Δsad ΔgabD | Current invention |
| pKD13 | Template plasmid with Kan$^R$ gene and FLP recognition target | Datsenko and Wanner, 2000 |
| pKD46 | λ-Red recombinase expression helper plasmid, oriR101, repA101(ts), Amp$^R$ | Datsenko and Wanner, 2000 |
| pCP20 | FLP recombinase helper plasmid, ts-rep, Amp$^R$, Cm$^R$ | Datsenko and Wanner, 2000 |
| pMD19-T SIMPLE | Cloning vector, Amp$^R$ | TaKaRa Bio Inc |
| pBBR1MCS-2 | Expression plasmid, Kan$^R$ | Kovach et al., 1995 |
| pCK3 | A 7.5 kb genomic DNA fragment of *C. kluyveri* inserted into pBluescript SK, containing orfZ, cat1, sucD and 4hbD, Amp$^R$ | Söhling and Gottschalk, 1996 |
| pBHR68 | phaCAB expression plasmid, Amp$^R$ | Spiekermann et al., 1999 |
| p68orfZ (SEQ ID NO 1) | orfZ gene inserted into pBHR68, Amp$^R$ | Current invention |
| pEn (SEQ ID NO 2) | Expression plasmid, $P_{pdc}$, pMD19-T SIMPLE derived | Current invention |
| pEnH1 (SEQ ID NO 3) | phaCAB operon inserted into pEn | Current invention |
| pEnRecA (SEQ ID NO 4) | recA gene inserted into pEn | Current invention |
| pKD46EnRecA (SEQ ID NO 5) | $P_{pdc}$-recA inserted into pKD46 | Current invention |
| pEnH5 (SEQ ID NO 6) | sucD-4hbD inserted into pEn | Current invention |
| pMCSH5 (SEQ ID NO 7) | $P_{pdc}$-sucD-4hbD inserted into pBBR1MCS-2 | Current invention |

E. coli MG1655 was kindly donated by Prof. Uwe Sauer, Institute of Molecular Systems Biology, ETH Zurich, Switzerland. E. coli JM109 was purchased from TaKaRa Bio Inc (Shiga, Japan) and used as the cloning host. The SSADH knockout mutants of E. coli JM109 were constructed according to the method described below. The recA deficient E. coli JM109 strains were used to ensure the plasmid stability and stable expression of heterologous genes for PHA accumulation. All E. coli strains were cultivated in Luria-Bertani medium containing 5 g per liter yeast extract, 10 g per liter Bacto tryptone, and 10 g per liter NaCl.

1.2. Plasmid Construction

Standard procedures or manufacturers' instructions were used for molecular cloning experiments. Plasmid isolation and DNA purification kits were purchased from Qiagen (Shanghai, China). Restriction enzymes and DNA modifying enzymes were provided by MBI Fermentas (Vilnius, Lithuania). Table 2 lists the primers used for polymerase chain reactions (PCR) in this invention.

TABLE 2

Primers used in the examples of this invention (restriction endonuclease digestion sites were underlined)

| Primers | Sequence |
|---|---|
| SadF (SEQ ID NO 8) | 5'-ATGACCATTACTCCGGCAACTCATGCAATTTC GATAAATCCTGCCACGGGGTGTAGGCTGGAGCTGC TTCG |
| SadR (SEQ ID NO 9) | 5'-CCCGAAACGCGGTCATTTCTGGGGTAACATTC GCCAGAACCGTTGGCGGAATTCCGGGGATCCGTCG ACC |
| GabDF (SEQ ID NO 10) | 5'-ATGAAACTTAACGACAGTAACTTATTCCGCC AGCAGGCGTTGATTAACGGGTGTAGGCTGGAGC TGCTTCG |
| GabDR (SEQ ID NO 11) | 5'-GCCTTTCTCCAGCGCATCGGCAATATGCTCT TCCACTTTTGCTACCGCTTATTCCGGGGATCCGT CGACC |
| RecAF (SEQ ID NO 12) | 5'-GTGAGCTCGTATTACCCGGCATGACAGGAG |
| RecAR (SEQ ID NO 13) | 5'-GTGAGCTCGGGATGTTGATTCTGTCATGGC |
| H1#F (SEQ ID NO 14) | 5'-GGATCCAAGGAGATATACCATGGCGACCGG CAAAGGCGC |
| H1#R (SEQ ID NO 15) | 5'-AAGCTTAGGTCAGCCCATATGCAGGC |
| H5#F (SEQ ID NO 16) | 5'-GGATCCAAGGAGATATACCATGAGTAATGA AGTATCTATAAAAG |
| H5#R (SEQ ID NO 17) | 5'-AGATCTCTCTTAAGATGGGATATTTAATG |

Figure 2:
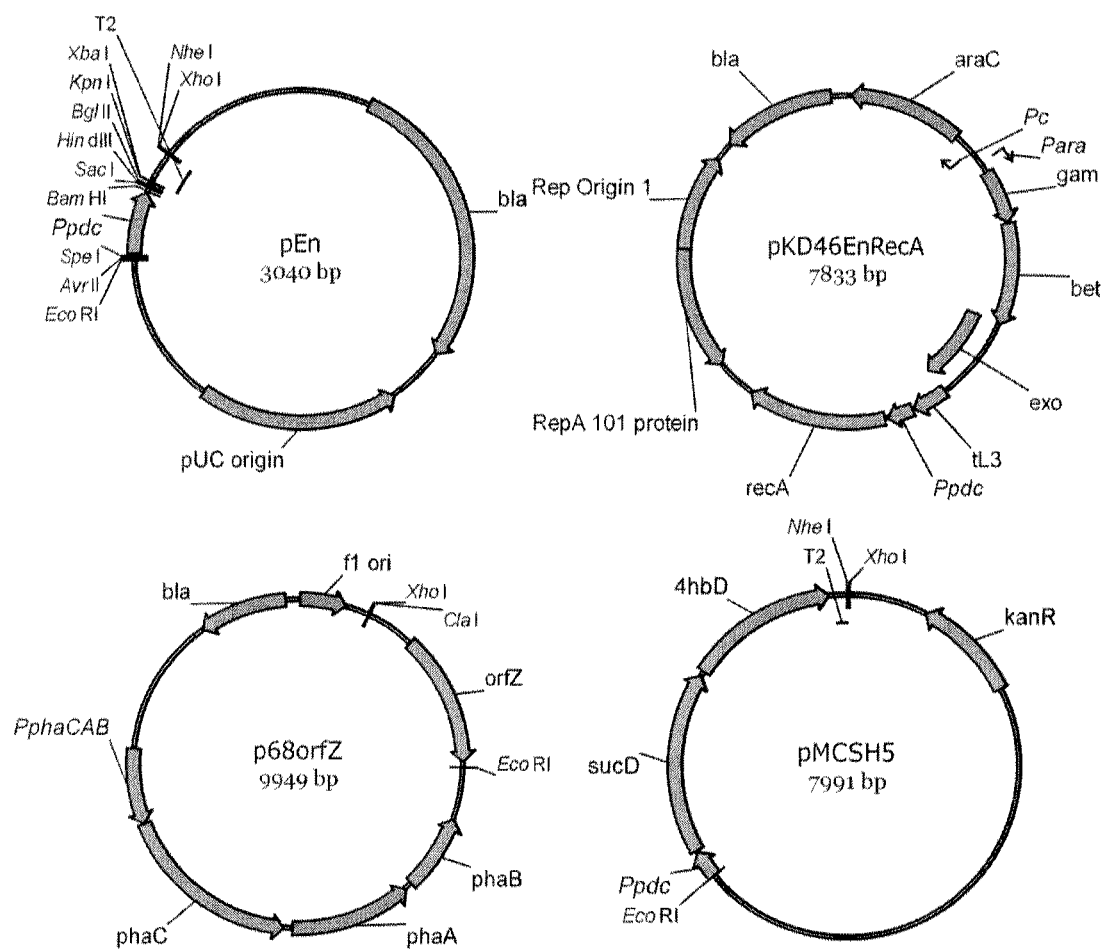
*
FIG. 2 shows the structures of the plasmids used in *E. coli* in the above example.

To construct the expression vector pEn, a chemically synthesized DNA fragment containing the pyruvate decarboxylase promoter ($P_{pdc}$) (Li et al., 2009), multiple cloning sites, and the rrnBT2 transcriptional terminator (Dykxhoorn et al., 1996) was ligated to pMD19-T SIMPLE vector by TA cloning. For assembling genes in a stepwise manner, EcoRI-AvrII-SpeI restriction sites were designed upstream of $P_{pdc}$, and NheI-XhoI restriction sites were designed downstream of rrnBT2 in pEn, as shown in FIG. 2.

The recA gene of E. coli MG1655 was amplified from the genomic DNA using primers RecAF/RecAR. The PCR product was ligated to pMD19-T SIMPLE for sequencing, then the recA gene was subcloned into pEn to generate pEnRecA. Finally, the recA gene along with $P_{pdc}$ and rrnBT2 were excised from pEnRecA using AvrII/NheI and then ligated to pKD46 digested with Eco130I through blunt end ligation to generate pKD46EnRecA, as shown in FIG. 2.

The P(3HB) synthesis operon (phaCAB) was amplified from pBHR68 using primers H1#F/H1#R and subcloned into pEn to construct pEnH1. The sucD-4-hbD operon was amplified from pCK3 using primers H5#F/H5#R and subcloned into pEn to generate pEnH5. To construct pMCSH5, sucD-4-hbD with $P_{pdc}$ and rrnBT2 were excised from pEnH5 using EcoRI/XhoI and cloned into pBBR1MCS-2 digested with the same restriction enzymes (FIG. 2). To construct p68orfZ, a 1.8-kb ClaI/EcoRI restriction fragment comprising orfZ gene of C. kluyveri was isolated from pCK3 and cloned into pBHR68 cut with the same restriction enzymes (FIG. 2).

1.3. Gene Knockout Procedures

PCR-mediated gene deletions in E. coli JM109 were performed with some modifications according to the method reported previously (Datsenko and Wanner, 2000; Baba et al., 2006). Oligonucleotides used for the generation of gene deletion fragments are shown in Table 2, comprising 50-nt-long homology extensions and 20-nt priming sequences for the template, pKD13. PCR fragments containing $Kan^R$ gene flanked by FLP recognition target (FRT) sites and 50-bp homologies to adjacent chromosomal sequences, were generated. PCR reactions were carried out in 25 µl mixtures containing 1.25 U of TaKaRa Ex Taq polymerase, 0.5 µg pKD13 DNA, 1.0 µM of each primer, and 200 µM each dNTPs. The mixtures were incubated at 94° C. for 5 min, followed by 30 cycles at 94° C. (30 s), 58° C. (30 s), and 72° C. (1 min), and followed by a final extension time of 10 min at 72° C.

Recombinants carrying pKD46EnRecA were grown in Luria-Bertani medium at 30° C. to an $OD_{600}$=0.2-0.3, then transferred to 37° C. and induced with 0.3% L-arabinose for 1 h. Cells were made electrocompetent by concentrating 100-folds and washing twice with ice-cold 10% glycerol. For electroporation, 50 µl of competent cells were mixed with 200 ng of the PCR products, and then electroporated at 1.25 kV with 25 µF and 200Ω in an ice-cold 0.1 cm cuvette (Bio-Rad Inc., USA), followed by the addition of 1 ml of Luria-Bertani medium. After incubation at 37° C. for 2 h, cells were spread on $Kan^R$ plates at 37° C. for 24 h. The positive colonies were selected by PCR verification.

The $Kan^R$ gene was eliminated by using plasmid pCP20 expressing the FLP recombinase, which acts on the directly repeated FRT sites. Briefly, the $Kan^R$ mutants were transformed with pCP20 and spread on AmpR plates at 30° C. for 24 h. Colonies were purified without antibiotics at 42° C. and then tested for loss of all resistances. The majority lost the FRT-flanked $Kan^R$ gene and the FLP helper plasmid simultaneously. All gene deletions were confirmed by PCR analysis and sequencing.

1.4. Culture Conditions for PHA Accumulation

Plasmids pMCSH5 and p68orfZ were co-transformed into E. coli JM109 and its SSADH deficient mutants by electroporation. Subsequently, the recombinants were cultivated for PHA accumulation studies.

The seed culture was grown at 37° C. in Luria-Bertani medium for 12 h at 200 rpm on a rotary shaker. For shake flask studies, seed culture was inoculated into 500 ml shake flasks containing 50 ml Luria-Bertani medium supplemented with 20 g per liter glucose at an inoculation volume of 4%. Optionally, α-ketoglutarate, oxaloacetate, citrate or succinate was added to LBG medium at a required concentration (see Table 3). For fermentor studies, seed culture was inoculated into a 6-liter fermentor (NBS 3000, New Brunswick, USA) at 10% inoculation volume with an operating volume of 3 liter. The starting fermentation medium was the same as that of shake flask except higher yeast extract concentration (10 g per liter) was needed. The pH in the fermentor culture was maintained at 7.0 by automatic addition of 5 M NaOH and 5 M $H_2SO_4$. Dissolved oxygen (DO) was provided by injecting filtered air at a flow rate of 3 liter per min and was maintained at 20% of air saturation by automatically adjusting the agitation rate from 200 to 800 rpm. In all cases, a final concentration of 50 µg per ml kanamycin and 100 µg per ml ampicillin were added to the medium to maintain the stability of pMCSH5 and p68orfZ.

1.5. Analytical Methods

Bacteria were harvested by centrifugation at 8,000×g for 10 min and then washed with distilled water. Cell dry weight was measured after vacuum lyophilization. PHA content and composition were analyzed by gas chromatography (Hewlett-Packard model 6890) after methanolysis of lyophilized cells in chloroform. P(3HB) and γ-butyrolactone (Sigma-Aldrich) were used as standards. The concentration of glucose was determined by HPLC (P2000, AS3000, Thermo Spectra System, USA) equipped with an ion exchange column (Aminex® HPX-87H, 7.8×300 mm, Bio-Rad) and a refractive index detector (RI-150, Thermo Spectra System, USA). A mobile phase of 2 mM $H_2SO_4$ at a 0.5 ml per min flow rate was used.

1.6. The Extraction and Physical Characterization of PHA

Intracellular PHA polymers were isolated from the lyophilized cells by hot chloroform in screw-capped tubes at 100° C. for 4 h. The chloroform and bacterial suspension was filtered through Whatman paper and precipitated in an excess of 10 volumes of ice-cold n-hexane.

Differential scanning calorimetry (DSC) data were recorded in the temperature range of −80 to 200° C. under a nitrogen flow rate of 50 ml per min on a TA instruments (DSC-2910 Differential Scanning calorimeter) according to the method reported previously (Luo et al. 2006).

For mechanical properties assay, PHA samples were turned into films by the conventional solvent-casting method, and then the PHA films were cut into dumbbell-shaped specimens with a width of 4 mm and a thickness of approximately 100 µm. The stress-strain measurements of films were carried out using a CMT-4000 universal testing machine (Shenzhen SANS, China) at room temperature. The speed of the cross-head was 50 mm per min (Luo et al. 2006).

2. Results 2.1. Construction of a Constitutive Expression Vector in *E. coli*

A chemically synthesized DNA fragment comprising $P_{pdc}$ with multiple cloning sites and rrnBT2 terminator sequence was ligated to pMD19-T SIMPLE vector to generate the expression plasmid pEn. Restriction sites were introduced upstream of the promoter and downstream of the terminator to facilitate gene assembling. For functional analysis of pEn, the P(3HB) synthesis operon phaCAB from *R. eutropha* was inserted into the vector to construct pEnH1, and then *E. coli* JM109/pEnH1 and *E. coli* JM109/pBHR68 were cultivated in Luria-Bertani medium supplemented with 20 g liter-1 glucose for 24 h for evaluation on the P(3HB) production ability. *E. coli* JM109 containing plasmid pBHR68 harboring phaCAB was used as the control. *E. coli* JM109 harboring pEnH1 could reach a 8.49 g liter-1 cell dry weight containing 71.4 wt % P(3HB), which was compatible to that of the control strain harboring pBHR68 that produced 8.90 g liter-1 cell dry weight consisting of 75.2 wt % P(3HB) when cultivated under the same growth conditions.

Thus, the pyruvate decarboxylase promoter ($P_{pdc}$) was proven to be able to transcribe constitutively with high efficiency in *E. coli*. By contrast, the plasmid skeleton containing 4hbD and sucD genes in U.S. Pat. No. 6,117,658 is pBlueScirpt, which contains lac promoter, and thus requires addition of isopropylthiol-β-D-galactoside for induction. This will require additional procedures and costs than using as $P_{pdc}$ in the current invention. Further, the current invention has at least the advantage of enhancing 4HB content in the final P(3HB-co-4HB) product.

2.2. Gene Deletions in *E. coli* JM109

To conduct gene deletions in the recA deficient *E. coli* JM109, a λ phage Red recombinase and RecA helper plasmid pKD46EnRecA was constructed. When recombinant harboring pKD46 was electrotransformed with PCR products, there was no colony growth on $Kan^R$ plates. By contrast, several colonies grew on $Kan^R$ plates using pKD46EnRecA as a helper plasmid. Further experiments including PCR analysis and antibiotic test showed that $Kan^R$ gene was indeed inserted into the target position of chromosome. Then the $Kan^R$ gene was eliminated by the FLP-recombination mediated by pCP20. Finally, the gene deleted mutant without any antibiotic resistance was obtained after non-selective purification at 42° C. Using this procedure, single and double sad/gabD deletion mutants of *E. coli* JM109 were constructed and designated as JM109S, JM109G, and JM109SG, which are deposited at the China General Microbiological Culture Collection Centre (Center No. 1, Institute of Microbiology Chinese Academy of Science, Beichen West Aveune, Chaoyang District, Beijing 100101, China) with deposition numbers CGMCC Nos. 4531 for *E. coli* JM109S, 4530 for *E. coli* JM109G, and 4532 for *E. coli* JM109SG, and were deposited on 7 Jan. 2011. The bacteria were confirmed to be active and alive at deposition. Both PCR analysis and sequencing confirmed the successes of gene deletions in the mutants.

2.3. Influence of sad and gabD Knockout on P(3HB-co-4HB) Production from Glucose To produce P(3HB-co-4HB) from glucose, the P(3HB) synthesis pathway of *R. eutropha* and the succinate degradation pathway of *C. kluyveri* were introduced into *E. coli* simultaneously. Six genes involved in the synthetic pathway (FIG. 1) were co-expressed using a double plasmid system p68orfZ and pMCSH5 to stabilize the expression. In p68orfZ, phaCAB and orfZ were transcribed from their own promoters constitutively. Similarly, in pMCSH5, 4hbD-sucD was driven by $P_{pdc}$ constitutively. The constitutive gene transcription provides desirable protein expression level for PHA production, and avoided the use of expression inducers such as isopropyl-β-D-thiogalactopyranoside (IPTG). The application of these plasmids achieved high-level expression of heterologous genes, evidenced by the results in Table 3.

TABLE 3

P(3HB-co-4HB) production from unrelated carbon sources by different *E. coli* strains

| *E. coli* strains | Carbon sources | CDW (g liter$^{-1}$) | P(3HB-co-4HB) (wt %) | 4HB monomer (mol %) |
|---|---|---|---|---|
| JM109 | G | 8.95 ± 0.14 | 72.44 ± 0.78 | Trace |
| JM109G | G | 9.40 ± 0.15 | 68.56 ± 1.21 | 0.79 ± 0.08 |
| JM109S | G | 9.74 ± 0.10 | 63.26 ± 1.10 | 8.79 ± 0.51 |
| JM109SG | G | 9.39 ± 0.22 | 65.51 ± 2.42 | 11.12 ± 0.44 |
| JM109SG | G + KG (0.5)* | 8.92 ± 0.28 | 66.31 ± 2.29 | 12.81 ± 2.43 |
| JM109SG | G + KG (1.0) | 8.97 ± 0.14 | 67.47 ± 1.79 | 18.00 ± 0.86 |
| JM109SG | G + KG (1.5) | 9.70 ± 0.02 | 65.39 ± 0.98 | 22.61 ± 0.49 |
| JM109SG | G + KG (2.0) | 9.62 ± 0.22 | 66.91 ± 1.47 | 20.44 ± 2.32 |

TABLE 3-continued

P(3HB-co-4HB) production from unrelated carbon sources by different E coli strains

| E. coli strains | Carbon sources | CDW (g liter$^{-1}$) | P(3HB-co-4HB) (wt %) | 4HB monomer (mol %) |
|---|---|---|---|---|
| JM109SG | G + O (1.0) | 9.45 ± 0.11 | 63.43 ± 1.12 | 16.33 ± 0.71 |
| JM109SG | G + C (1.0) | 9.00 ± 0.05 | 63.65 ± 0.52 | 20.30 ± 1.17 |
| JM109SG | G + S (1.0) | 9.00 ± 0.12 | 61.07 ± 0.47 | 11.63 ± 1.83 |
| JM109SG | G + S (2.0) | 9.45 ± 0.13 | 61.31 ± 0.83 | 13.47 ± 1.71 |

In Table 3, the recombinants harboring p68orfZ and pMCSH5 were cultivated in Luria-Bertani medium containing 2% (w/v) glucose or 2% (w/v) glucose plus a various concentration of α-ketoglutarate, oxaloacetate, citrate or succinate at 37° C. for 48 h as described in the above section "1. Materials and methods". Data shown are the average and standard deviation of three parallel experiments. Abbreviations: G, glucose; KG, α-ketoglutarate; O, oxaloacetate; C, citrate; S, succinate; CDW, cell dry weight. * compound concentration, indicated as g per liter.

The two plasmids p68orfZ and pMCSH5 were co-transformed into E. coli JM109 and its SSADH deficient mutants for PHA accumulation studies. All strains harboring p68orfZ and pMCSH5 reached 9 g per liter cell dry weight containing over 60% PHA after 48 h cultivation in Luria-Bertani medium supplemented with 20 g per liter glucose. Regarding the 4HB monomer content, only marginal levels of 4HB could be detected in the wild type. When only glucose is used and when gabD gene was deleted, 4HB content in the P(3HB-co-4HB) product was observed. A much higher molar fraction of 8.79 mol % 4HB in the copolymer was produced by the sad gene deleted mutant. The sad and gabD genes deleted mutant showed the highest 4HB content in the P(3HB-co-4HB) product, in which the 4HB level reached to 11.1 mol % in the copolymer (Table 3).

2.4. Influence of TCA Intermediates on P(3HB-co-4HB) Production

In tricarboxylic acid cycle, succinyl-CoA was generated via the oxidation of α-ketoglutarate (FIG. 1). Thus, different amounts of α-ketoglutarate were added to the culture to study the effect of α-ketoglutarate on PHA and 4HB monomer formation (Table 3). As shown in Table 3, 4HB monomer content in the P(3HB-co-4HB) product was enhanced with increasing of α-ketoglutarate concentrations in the cultures. When α-ketoglutarate was added at 1.5-2 g liter-1, the 4HB monomer content increased from 11.1 mol % to approximately 22 mol %. However, it was found that high concentration of α-ketoglutarate over 2 g per liter started to inhibit cell growth (data not shown) and therefore is not preferred.

Effects of other TCA intermediates including oxaloacetate, citrate and succinate on polymer composition were investigated (Table 3). The addition of 1.0 g per liter of oxaloacetate increased 4HB monomer content to 16.3 mol %, while the addition of 1.0 g per liter of citrate led to a significant increase of 4HB to 20.3 mol %. However, strains showed no obvious growth when oxaloacetate was added at 2.0 g per liter, and the addition of 2.0 g per liter of citrate decreased cell dry weight and thus reduced PHA accumulation (data not shown). The addition of succinate at 1.0 or 2.0 g per liter had no outstanding improvement on 4HB monomer content, possibly indicating the flux toward succinyl-CoA from succinate was in a low level under the aerobic growth condition.

2.5. P(3HB-co-4HB) Production in 6 Liter Fermentor

Figure 3:
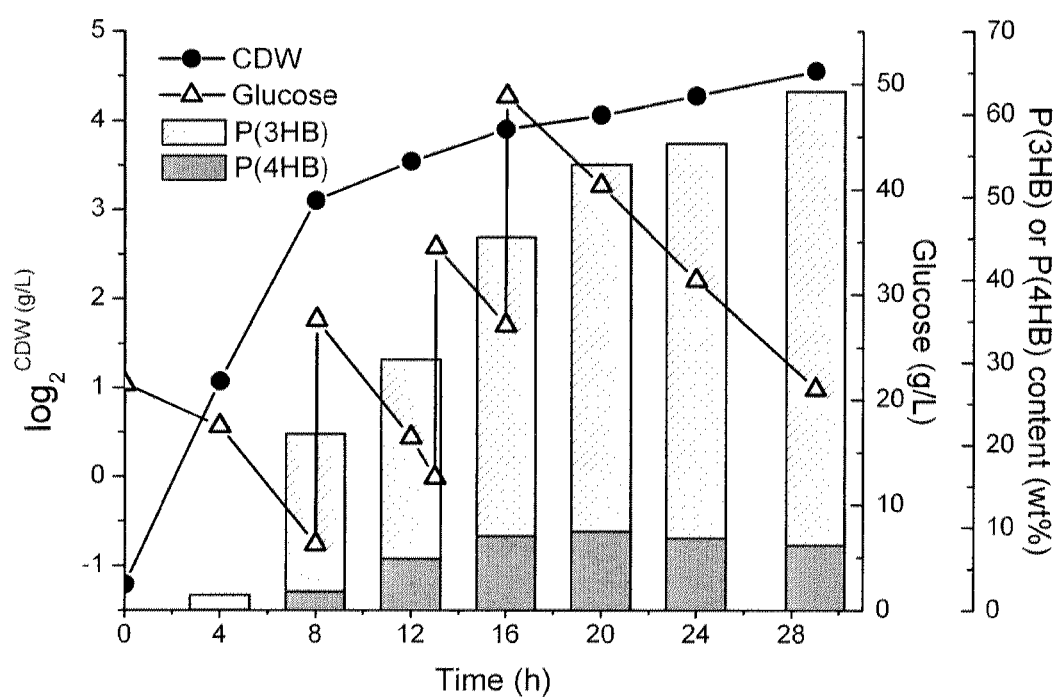
FIG. 3 shows the cell dry weight, PHA content, 4HB monomer content and glucose consumption profile of the engineered *E. coli* in FIG. 2.

The SSADH gene double deleted mutant E. coli JM109SG harboring p68orfZ and pMCSH5 was grown in a 6-liter NBS fermentor using a fed-batch process, in which glucose was supplied as the carbon source. The recombinant strain produced 23.5 g per liter cell dry weight containing 62.7% P(3HB-co-12.5 mol % 4HB) after 65 g per liter glucose was consumed in 29 h (FIG. 3). The 4HB monomer content reached to the highest level of over 20 mol % in the exponential growth phase and then decreased to 12.5 mol %. Both the PHA and final 4HB monomer content were similar with that of the shake flask cultures (FIG. 3).

2.6. Physical Characterization of P(3HB-co-4HB) Produced by E. coli

Thermal and mechanical properties of P(3HB) and P(3HB-co-4HB) with different 4HB fractions (11.1 or 18.0 mol %) were studied (Table 4). In Table 4, the 4HB monomer content was determined by GC. The addition of 4HB units into copolymers lowered the melting temperatures ($T_m$) and apparent heat of fusion ($\Delta H_m$) compared to that of the P(3HB) homopolymer. Furthermore, the glass transition temperature ($T_g$) decreased from 0.8° C. to −9.2° C. as the 4HB content increased from 0 to 18.0 mol %. Changes on mechanical properties includes remarkable increase in the elongation at break (4) from 5.9% to approximate 700% when the 4HB content fraction increased from 0 to 11.1 or 18.0 mol %. Tensile strength ($\sigma_t$) of P(3HB-co-11.1 mol % 4HB) was similar to that of P(3HB) homopolymer, while $\sigma_t$ of P(3HB-co-18 mol % 4HB) decreased to 9.9 Mpa. By contrast, P(3HB) homopolymer showed typical brittle features, while the P(3HB-co-4HB) copolymers exhibited behaviors of thermoplastic elastomers. The results showed suitable application properties for copolymer produced from glucose alone according to the current invention.

TABLE 4

Physical characterization of P(3HB-co-4HB) produced by the current invention

| | Thermal properties | | | Mechanical properties | |
|---|---|---|---|---|---|
| PHA samples | $T_m$ (° C.) | $\Delta H_m$ (J/g) | $T_g$ (° C.) | $\sigma_t$ (MPa) | $\epsilon_b$ (%) |
| P(3HB) | 177.3 | 83.0 | 0.8 | 20.4 | 5.9 |
| P(3HB-co-11.1 mol % 4HB) | 131.5 | 39.9 | −4.4 | 20.3 | 698 |
| P(3HB-co-18.0 mol % 4HB) | 127.9 | 19.2 | −9.2 | 9.9 | 729 |

3. Discussion

In U.S. Pat. No. 6,117,658, the 4HB monomer content in the P(3HB-co-4HB) product is at most 5 mol %, which is too low to have any improvement on the thermal and mechanical properties of the copolymer. By contrast, in the current invention, engineered E. coli strains were developed which accumulated P(3HB-co-4HB) with high 4HB monomer content from unrelated carbon sources.

Two compatible plasmids p68orfZ and pMCSH5 were constructed to express the six heterologous genes involved in P(3HB-co-4HB) biosynthesis pathway in E. coli. When cultivated with glucose, E. coli JM109 harboring p68orfZ and pMCSH5 accumulated large amounts of P(3HB) in the cells accompanying with trace amount of 4HB monomer. In the 4HB production pathway, succinyl-CoA was first converted to SSA, which could be degraded to succinate by SSADH, thus competing with 4HB-CoA biosynthesis, leading to the reduced metabolic flux to 4HB production. In order to obtain an effective production of 4HB-CoA from succinyl-CoA, the native SSADH genes of E. coli should be inactivated.

In the current invention, a modified helper plasmid pKD46EnRecA was constructed to co-express RecA and λ Red recombinase simultaneously. With the aids of pKD46EnRecA, positive colonies were obtained after electrotransformation using KanR containing PCR products in *E. coli* JM109. Results above indicated that the RecA and λ Red recombinase containing helper plasmid could be used for gene knockout in recA deficient bacterial strains. Using the modified method, the single and double SSADH deleted mutants of *E. coli* JM109 were constructed.

Shake flask studies employing *E. coli* JM109 SSADH deleted mutants were performed to evaluate the effect of SSADH knockout on polymer composition. The deletion of gabD gene resulted in a slight increase on 4HB accumulation, while the deletion of sad gene enhanced 4HB content more significantly. The SSADH double mutant showed the highest 4HB producing ability (Table 3). These results indicated that the SSADH inactivation could improve 4HB accumulation from succinyl-CoA, probably due to the blockage of succinate formation from SSA (FIG. 1). Although both sad and gabD genes encode SSADH, it was believed that sad functions as a valve in preventing the accumulation of toxic SSA. The results above may indicate that, though not bound to any theory of the working of this invention, when SSA was accumulated, sad gene was strongly induced. It appears that Sad plays a major role in metabolize SSA, since the sad mutant showed the most obvious improvement on 4HB accumulation. GabD may also catalyze the degradation of SSA, yet functioned as a secondary factor.

The addition of appropriate amounts of α-ketoglutarate or citrate enhanced the 4HB monomer content to more than 20 mol % in shake flask cultures, probably due to a favorable succinyl-CoA supply (Table 3). A sufficient supply of succinyl-CoA assisted in obtaining a copolymer consisting of high 4HB monomer content. The addition of oxaloacetate also promoted 4HB accumulation, yet the increase was lower than that of the increase induced by α-ketoglutarate or citrate. Considering the cost of these TCA intermediates, citrate may be the best choice for enhancing 4HB accumulation in large-scale industrial processes.

In a 6 liter NBS fermentor culture, the engineered strain also accumulated P(3HB-co-4HB) from glucose. In a growth period of 12-16 h, 4HB monomer content reached the highest level, and then decreased to about 12 mol % (FIG. 3). During the exponential growth phase, the strain showed a high growth rate and the tricarboxylic acid cycle may be in an active state to supply sufficient succinyl-CoA for the 4HB-CoA biosynthesis process, thus, leading to higher 4HB monomer content.

The incorporation of 4HB monomer into copolymers changed the thermal and mechanical properties of PHA. The melting temperature, apparent heat of fusion and glass-transition temperature of P(3HB-co-4HB) copolymers were lower than that of P(3HB) homopolymer (Table 4). Moreover, the elongation at break increased dramatically as the incorporation of 4HB units. The P(3HB) homopolymer exhibits rigid and brittle feature, which restricted its applications. 4HB units in P(3HB-co-4HB) copolymers reduced the crystallinity of P(3H13), thus, the copolymer film showed considerable flexibility and toughness (Table 4). P(3HB-co-4HB) produced in this study possesses desirable mechanical properties for various potential applications.

To conclude, in the current invention, P(3HB-co-4HB) could be produced from unrelated carbon sources by a metabolically engineered recombinant *E. coli* having high 4HB monomer content in the range of 8.8 to 23 mol % according to the current invention. With glucose as the carbon source, 4HB monomer content reached over 8 mol % in both shake flask and fermentor studies, which is the highest 4HB content so far as reported for P(3HB-co-4HB) from unrelated carbon sources in *E. coli*.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

References (the Content are Fully Incorporated into the Current Specification):

a) Baba, T., Ara, T., Hasegawa, M., Takai, Y., Okumura, Y., Baba, M., Datsenko, K. A., Tomita, M., Wanner, B. L., Mori, H., 2006. Construction of *Escherichia coli* K-12 in-frame, single-gene knockout mutants: the Keio collection. Mol. Syst. Biol. 2, 1-11.

b) Datsenko, K. A., Wanner, B. L., 2000. One-step inactivation of chromosomal genes in *Escherichia coli* K-12 using PCR products. Proc. Natl. Acad. Sci. USA. 97, 6640-6645.

c) Dykxhoorn, D. M., St. Pierre, R., Linn, T., 1996. A set of compatible tac promoter expression vectors. Gene. 177, 133-136.

d) Kovach, M. E., Elzer, P. H., Hill, D. S., Robertson, G. T., Farris, M. A., Roop II, R. M., Peterson, K. M., 1995. Four new derivatives of the broad-host-range cloning vector pBBR1MCS, carrying different antibiotic-resistance cassettes. Gene. 166, 175-176.

e) Li, Z. J., Cai, L., Wu, Q., Chen, G. Q., 2009. Overexpression of NAD kinase in recombinant *Escherichia coli* harboring the phbCAB operon improves poly(3-hydroxybutyrate) production. Appl. Microbiol. Biotechnol. 83, 939-947.

f) Luo, R. C., Chen, J. Y., Zhang, L., Chen, J. C., Chen, G. Q. 2006. Polyhydroxyalkanoates copolyesters produced by *Ralstonia eutropha* PHB-4 harboring a low-substrate-specificity PHA synthase PhaC2Ps from *Pseudomonas stutzeri* 1317. Biochem. Eng. J. 31, 218-225 g) Sauer, U., Canonaco, F., Heri, S., Perrenoud, A., Fischer, E., 2004. The soluble and membrane-bound transhydrogenases UdhA and PntAB have divergent functions in NADPH metabolism of *Escherichia coli*. J. Biol. Chem. 279, 6613-6619.

h) Söhling, B., Gottschalk, G., 1996. Molecular analysis of the anaerobic succinate degradation pathway in *Clostridium kluyveri*. J. Bacteriol. 178, 871-880.

i) Spiekermann, P., Rehm, B. H. A., Kalscheuer, R., Baumeister, D., Steinbüchel, A., 1999. A sensitive, viable-colony staining method using Nile red for direct screening of bacteria that accumulate polyhydroxyalkanoic acids and other lipid storage compounds. Arch. Microbiol. 171, 73-80.

The invention claimed is:

1. A recombinant host for manufacturing polyhydroxyalkanoate, wherein
   native succinate semialdehyde dehydrogenase gene is removed from said recombinant host; and
   a first plasmid and a second plasmid including genes for manufacturing the polyhydroxyalkanoate are transformed to the recombinant host, the first plasmid includes 4-hydroxybutyrate-CoA:CoA transferase gene (orfZ gene), β-ketothiolase gene (phaA gene), NADPH-dependent acetoacetyl-CoA reductase gene (phaB gene), and polyhydroxyalkanoate synthase gene (phaC gene), and the second plasmid includes succinate semialdehyde dehydrogenase gene (sucD gene) and 4-hydroxybutyrate dehydrogenase gene (4hbD gene);
   characterized in that the second plasmid further includes pyruvate decarboxylase promoter ($P_{pdc}$);
   wherein the first plasmid has the sequence of SEQ ID NO: 1 and the second plasmid has the sequence of SEQ ID NO: 7.

2. The recombinant host of claim 1, wherein the polyhydroxyalkanoate is a copolymer of 3-hydroxybutyrate and 4-hydroxybutyrate.

3. The recombinant host of claim 1, wherein the host is *Escherichia coli*.

4. The recombinant host of claim 3, wherein the native succinate semialdehyde dehydrogenase gene is sad and/or gabD genes.

5. The recombinant host of claim 4, wherein the native succinate semialdehyde dehydrogenase gene is sad gene.

6. The recombinant host of claim 4, wherein the native succinate semialdehyde dehydrogenase gene is sad and gabD genes.

* * * * *

SEQUENCE LISTING

<160> NUMBER OF SEQ ID NOS: 17

<210> SEQ ID NO 1
<211> LENGTH: 9949
<212> TYPE: DNA
<213> ORGANISM: Artificial sequence
<220> FEATURE:
<223> OTHER INFORMATION: p68orfZ plasmid

<400> SEQUENCE: 1

| | | | | | |
|---|---|---|---|---|---|
| cacctgacgc | gccctgtagc | ggcgcattaa | gcgcggcggg | tgtggtggtt acgcgcagcg | 60 |
| tgaccgctac | acttgccagc | gccctagcgc | ccgctccttt | cgctttcttc ccttcctttc | 120 |
| tcgccacgtt | cgccggcttt | ccccgtcaag | ctctaaatcg | gggctccct ttagggttcc | 180 |
| gatttagtgc | tttacggcac | ctcgacccca | aaaaacttga | ttagggtgat ggttcacgta | 240 |
| gtgggccatc | gccctgatag | acggttttc | gccctttgac | gttggagtcc acgttcttta | 300 |
| atagtggact | cttgttccaa | actggaacaa | cactcaaccc | tatctcggtc tattcttttg | 360 |
| atttataagg | gattttgccg | atttcggcct | attggttaaa | aaatgagctg atttaacaaa | 420 |
| aatttaacgc | gaattttaac | aaaatattaa | cgcttacaat | ttccattcgc cattcaggct | 480 |
| gcgcaactgt | tgggaagggc | gatcggtgcg | ggcctcttcg | ctattacgcc agctggcgaa | 540 |
| aggggggatgt | gctgcaaggc | gattaagttg | ggtaacgcca | gggttttccc agtcacgacg | 600 |
| ttgtaaaacg | acggccagtg | aattgtaata | cgactcacta | tagggcgaat tgggtaccgg | 660 |
| gccccccctc | gaggtcgacg | gtatcgataa | gcttttaggt | caatgcagcg gctgtatttc | 720 |
| agctaagtat | acagtacagg | atatagtgga | aggttccata | aaaaacgaaa ttcctgaaat | 780 |
| aaaatcagta | gaggttatag | actatataga | tgaagatact | ttgaatatgg caagaaaaat | 840 |
| attaagtaag | catcataggt | aaggtgagta | tattttgtat | gtaggaatta atatattgcgg | 900 |
| aggatgtaat | cctaaatatg | atagaaaaca | atttctatat | aatttacaac aacaatttaa | 960 |
| gtataatttt | gaaacagtgg | ctccagataa | aacttatgat | atagttatag ttttatgtgg | 1020 |
| atgtactagc | tgctgcgttg | atcatagtaa | gcttaagttt | aagcttgaaa aaatattggt | 1080 |
| aaaatccgaa | gaagatttta | gtgtggtaaa | aagtatattg | aataagtatt taacaagaca | 1140 |
| ggatagggag | gagataactt | ttatggagtg | ggaagagata | tataaagaga aactggtaac | 1200 |
| tgcagaaaaa | gctgtttcaa | aaatagaaaa | ccatagcagg | gtagttttg cacatgcagt | 1260 |
| aggagaaccc | gtagatttag | taatgcact | agtaaaaaat | aaggataatt atataggact | 1320 |
| agaaatagtt | cacatggtag | ctatgggcaa | aggtgaatat | acaaagagg gtatgcaaag | 1380 |
| acattttaga | cataatgctt | tatttgtagg | cggatgtact | agagatgcag taaattcagg | 1440 |
| aagagcagat | tatacacctt | gttttttcta | tgaagtgcca | agtttgttta agaaaaacg | 1500 |
| tttgcctgta | gatgtagcac | ttattcaggt | aagtgagcca | gataaatatg ctactgcag | 1560 |
| ttttggagtt | tccaatgact | ataccaagcc | agcagcagaa | agtgctaagc ttgtaattgc | 1620 |
| agaagtgaat | aaaaacatgc | caagaactct | tggagattct | tttatacatg tatcagatat | 1680 |
| tgattatata | gtggaagctt | cacacccatt | gttagaattg | cagcctccta aattgggaga | 1740 |
| tgtagaaaaa | gccataggag | aaaactgtgc | atctttaatt | gaagatggag ctactcttca | 1800 |
| gcttggaata | ggtgctatac | cagatgcggt | actttattc | ttaaagaaca aaagaattt | 1860 |
| aggaatacat | tctgagatga | tatcagatgg | tgtgatggaa | ctggtgaagg caggggttat | 1920 |
| caataacaag | aaaaagaccc | tccatccagg | caaatagtt | gtaacatttt taatgggaac | 1980 |

```
aaaaaaatta tatgattttg taaacaataa tccaatggta gaaacttatt ctgtagatta    2040
tgtaaataat ccactggtaa ttatgaaaaa tgacaatatg gtttcaataa attcttgtgt    2100
tcaagtagac ttaatgggac aagtatgttc tgaaagtata ggattgaaac agataagtgg    2160
agtgggaggc caggtagatt ttattagagg agctaatcta tcaaagggtg gaaaggctat    2220
tatagctata ccttccacag ctggaaaagg aaaagtttca agaataactc cacttctaga    2280
tactggtgct gcagttacaa cttctagaaa tgaagtagat tatgtagtta ctgaatatgg    2340
tgttgctcat cttaagggca aaactttaag aaatagggca agagctctaa taaatatcgc    2400
tcatccaaaa ttcagagaat cattaatgaa tgaatttaaa aagagatttt agaatttatt    2460
tatgattttt agttacactt tatatgaagg tgtaactaaa aataagaatt cgcccccgcg    2520
agggccgcgc tgcacgaaca tggtgctggc tgcgccgctg ccctgattct atgcccaaca    2580
aggcactaag aaaagcgacg gggcttaagg aaaacccggt gaattggcgc aaaaagcgag    2640
gaatgccgcg cgggcagaaa cgattcgcgg gccttgacgg cccgcgaaac gggcggcgaa    2700
acgaaacgcc cgccgccttg tgcgcctgca gcctcgcccc cgcgagggcc gcgctgcacg    2760
aacatggtgc tggctgcgcc gctgcccctga ttctatgccc aacaaggcac taagaaaagc    2820
gacggggctt aaggaaaacc cggtgaattg gcgcaaaaag cgaggaatgc cgcgcgggca    2880
gaaacgattc gcgggccttg acggcccgcg aaacgggcgg cgaaacgaaa cgcccgccgc    2940
cttgtgcgcc gcgctggctg caccgcaata cgcgggcgcc agcgccggct gccgactggt    3000
tgaaccaggc cggcaggtca gcccatatgc aggccgccgt tgagcgagaa gtcggcgccg    3060
gtcgagaaac cggactcctc cgacgacaac caggcgcaga tcgaggcgat ctcttccggc    3120
aggcccaggc gcttgaccgg gatcgtcgcg acgatcttgt cgagcacgtc ctggcggatc    3180
gccttgacca tgtcggtggc gatatagccc ggagagaccg tgttgacggt cacgcccttg    3240
gtcgccactt cctgcgccag tgccatggtg aagccatgca ggccggcctt ggcggtggag    3300
tagttggtct ggccgaactg gcccttctgc ccgttcaccg acgagatgtt gacgatgcgg    3360
ccccagccac ggtcggccat gccgtcgatc acctgcttgg tgacgttgaa cagcgaggtc    3420
aggttggtgt cgatcaccgc atcccagtcg gcgcgggtca tcttgcggaa caccacgtcg    3480
cgggtgatac cggcgttgtt gatcagcaca tcaacctcgc cgacctcgga cttgaccttg    3540
tcgaatgcgg tcttggtcga gtcccagtca gccacattgc cttccgaggc aatgaaatcg    3600
aagcccaggg ccttctgctg ctccagccac ttttcgcggc gcggcgagtt ggggccgcaa    3660
ccggccacca cacgaaagcc atccttggcc agccgctggc aaatggcggt tccgatacca    3720
cccatgccgc cggtcacata cgcaatgcgc tgagtcatgt ccactccttg attggcttcg    3780
ttatcgtcgc cgggtccgcg ccaaccgcgc gcggccccgg aaaaccccctt ccttatttgc    3840 gctcgactgc cagcgccacg cccatgccgc cgccgatgca cagcgaggcc aggcccttct    3900
tcgcgtcacg gcgcttcatc tcgtgcagca gcgtcaccag gatacggcag cccgacgcgc    3960
cgatcgggtg gccgatggcg atggcgccgc cgttcacatt gaccttggag gtgtcccagc    4020
ccatctgctg gtgcaccgcc agcgcctgcg cggcaaaggc ctcgttgatc tccatcaggt    4080
ccaggtcttg cggggtccac tcggcgcgcg acagggcgcg cttggaggcc ggcaccgggc    4140
ccatgcccat caccttggga tcgacaccgg cgttggcata gctcttgatc gtggccagcg    4200
gggtcaggcc cagttccttg gccttggccg ccgacatcac caccaccgcg gcggcgccgt    4260
cgttcaggcc cgaggcgttg gccgcggtca ccgtgccggc cttgtcgaag gcgggcttga    4320
ggccggacat gctgtccagc gtggcgccct ggcgcacgaa ctcgtcggtc ttgaaggcca    4380
```

```
ccgggtcgcc cttgcgctgc gggatcagca ccgggacgat ctcttcgtca aacttgccgg   4440
ccttctgcgc ggcttcggcc ttgttctgcg agccgacggc gaactcatcc tgcgcctcgc   4500
gtgtgatgcc gtattccttg ccacgttct cggcggtgat gcccatgtgg tactggttgt    4560
acacgtccca caggccgtcg acgatcatgg tgtcgaccag cttggcatcg cccatgcgga   4620
aaccatcgcg cgagcccggc agcacgtgcg gggcggcgct catgttttcc tggccgccgg   4680
ccaccacgat ctcggcgtcg cccgccatga tcgcgttggc ggccagcatc acggccttca   4740
ggcccgagcc gcacaccttg ttgatggtca tggccggcac catcgccggc aggccggcct   4800
tgatcgcggc ctggcgtgcg gggttctggc ccgaaccggc ggtcagcacc tggcccatga   4860
tgacttcgct cacctgctcc ggcttgacgc cggcgcgctc cagcgcggcc ttgatgacca   4920
cggcacccag ttccggtgcc gggatcttgg ccagcgagcc gccaaacttg ccgaccgcgg   4980
tgcgggcggc ggatacgatg acaacgtcag tcattgtgta gtcctttcaa tggaaacggg   5040
agggaacctg caggcctgcc ggcgccgtgc atgacgcacg ccggcactca tgcaagcgtc   5100
atgccttggc tttgacgtat cgcccaggcg cgggttcgat tgcgcgatag cgcgcattgc   5160
catagttggc gggcgcggcg cgtttcgcgc cggcctgccc ggccagccat gcggtccagt   5220
ccggccacca gctgccgtga tgctcgatgg cgccggccag ccattgctgc ggcgactccg   5280
gcagcgcatc gttagtccag tggctgcgct tgttcttggc cggcgggttg atcacaccgg   5340
cgatatggcc cgacgcaccc agcacgaagc gcagcttgtt cgccagcagc gcggtcgagg   5400
cataggccgc ggtccacggc acgatatggt cttcgcgcga gccgtagata taggtcggca   5460
cgtcgatgct ggccaggtcc accggcacgc cgcacacggt cagcttgccc ggtaccttga   5520
gctcgttctg caggtaggtg tggcgcaggt accagcagta ccacggcccc ggcaggttgg   5580
tggcgtcgcc gttccagaac agcaggtcga acggcaccgg cgtgttgccc ttcaggtagt   5640
tgtcgaccac gtagttccac accaggtcgt tcgggcgcaa gaacgagaag gtattggcca   5700
gctcaaggcc gcgcagcagc gcgcacggcg cgccggcgcc gccgcccagc gtggcctcgc   5760
gcaactgcac atgggccctcg tcgacaaaga cgtcgaggat gcccgtgtcg gcaaagtcca   5820
gcagcgtggt cagcagcgtg acgctggcgg ccgggtgctc gccgcgcgcg gccagcaccg   5880
ccagcgcggt cgagacaatg gtgccgccca cgcagaagcc gagcacgttg atcttgtcct   5940
ggccgctgat gtcgcgcgcg acttcgatgg cgcggatggc cgcgtgctcg atgtagtcgt   6000
cccaggtgct gccggccatg ctggcgtccg gattgcgcca cgacaccaga aacaccgtat   6060
gtccctgctc caccacatgg cgcaccacgc agctctccgg ctgcaggtcc aggatgtagt   6120
acttgttgat gcacggcggc accatcagca gcgggcgcgc gtgcaccttg tcggtcagcg   6180
gcttgtactg caacagctgg aagtactcgt tctcgaagac cacggcgcct tcggtcaccg   6240
cgacattgcg gccgacctca aacgcgctct cgtcggtctg cgagatcttg ccgcgtgtca   6300
ggtcttccat catgttgcgc acgccggcac gcagcgattc gccgcccgac tcgatcagca   6360
ggcgctgcgc ctcgggattg gtggcaagga agttggcggg cgacatcgca tcgacccatt   6420
gcgagatcgc gaagcggatg cgctggcggg tcttggcatc ggcctcgacg catcggcca   6480 gctcggtcaa ggcgcgcgca ttgagcaggt agaacgcggc agcgaagcga tatgggaggt   6540
tggtgcgcca tgcgtcgccg gcgaagcgcc ggtcgtgcag cggaccggtg gcctcggcct   6600
tgccctcggc catggcctgc cacagcgctg agaagtcctt catgtagcgc tgctggatat   6660
cacccagctg cgccggcgcg atcttgacgc ctgccagcgc atccaggccc ggaatgccgg   6720
acgcggccgc gtggccgttg ccttcagtgc cctgccactg gcgggaccat tccagccatg   6780
```

```
tggctggatc gaatggcccc ggcgtgacct tgaatggttg ggacttgcct tcctgcgtgg    6840
aagctgccgc gcctttgccg gtcgccatga tttgattgtc tctctgccgt cactattcga    6900
accggctccg ggcattgccc tggccggcac tttgcatggg gagatgctat ccgaatggac    6960
ccggcttgcg cctcccccaa agcgggaggg tctgccggca catctgccct ggaactggct    7020
ggaagccctc gaccgcacct gctgcggccg tggcttgcgt ccattccgat agcggctccc    7080
cttttatccg gcaagcgcga cattctcgca tggagacgcc atgcgctatg cttgccggag    7140
aaacctggga atcgtcagcg attccgagac atttgagtcc attgttgcct tgcaacgcac    7200
gcgctgtcaa tgcgggaatc cgcctcggca ctgcacgctt cccgacctac cggacggtat    7260
gcagcgctcg catctgccga ggccccagag cataggcgag aaggatgaat ttttgatgta    7320
catcgtggcc attggctggc tctacgtggc gctgatgatg cgatcaccg agcacaacgt    7380 ggtggcaggc gttgccacct tcctgatgta tggcatggcg ccggtggcgt ggtgctctac    7440
atcatgggca cgcccggccg ccgccgacgc aaggctgaag ccgagcgcgc gcaggcggcc    7500
aggggcaagg acgagtgagg cagcggcggg ctcagtccgc cagccagacc aggctggcca    7560
tgcggccggt cacgccatcg cgccgatagg agtagaagcg accggcgtcg gccacggtgc    7620
aggcgtcgcc gccgtagacc tcggtacagc cggcgcgcgc caggcgcgtg cgcgccagcg    7680
catagatgtc ggcaaggtac ttgcccgggg gatccactag ttctagagcg gccgccaccg    7740
cggtggagct ccagcttttg ttcccttttag tgagggttaa tttcgagctt ggcgtaatca    7800
tggtcatagc tgtttcctgt gtgaaattgt tatccgctca caattccaca acatacga     7860 gccgaagca taaagtgtaa agcctggggt gcctaatgag tgagctaact cacattaatt    7920
gcgttgcgct cactgcccgc tttccagtcg ggaaacctgt cgtgccagct gcattaatga    7980
atcggccaac gcgcggggag aggcggtttg cgtattgggc gctcttccgc ttcctcgctc    8040
actgactcgc tgcgctcggt cgttcggctg cggcgagcgg tatcagctca ctcaaaggcg    8100
gtaatacggt tatccacaga atcaggggat aacgcaggaa agaacatgtg agcaaaaggc    8160
cagcaaaagg ccaggaaccg taaaaaggcc gcgttgctgg cgtttttcca taggctccgc    8220
ccccctgacg agcatcacaa aaatcgacgc tcaagtcaga ggtggcgaaa cccgacagga    8280
ctataaagat accaggcgtt tcccctgga agctccctcg tgcgctctcc tgttccgacc    8340
ctgccgctta ccggatacct gtccgccttt ctcccttcgg gaagcgtggc gctttctcat    8400
agctcacgct gtaggtatct cagttcggtg taggtcgttc gctccaagct gggctgtgtg    8460
cacgaacccc ccgttcagcc cgaccgctgc gccttatccg gtaactatcg tcttgagtcc    8520
aacccggtaa gacacgactt atcgccactg gcagcagcca ctggtaacag gattagcaga    8580
gcgaggtatg taggcggtgc tacagagttc ttgaagtggt ggcctaacta cggctacact    8640
agaaggacag tatttggtat ctgcgctctg ctgaagccag ttaccttcgg aaaaagagtt    8700
ggtagctctt gatccggcaa acaaaccacc gctggtagcg gtggtttttt tgtttgcaag    8760
cagcagatta cgcgcagaaa aaaaggatct caagaagatc ctttgatctt ttctacgggg    8820
tctgacgctc agtggaacga aaactcacgt taagggattt tggtcatgag attatcaaaa    8880
aggatcttca cctagatcct tttaaattaa aaatgaagtt ttaaatcaat ctaaagtata    8940
tatgagtaaa cttggtctga cagttaccaa tgcttaatca gtgaggcacc tatctcagcg    9000
atctgtctat ttcgttcatc catagttgcc tgactccccg tcgtgtagat aactacgata    9060
cgggagggct taccatctgg ccccagtgct gcaatgatac gcgagaccc acgctcaccg    9120 gctccagatt tatcagcaat aaaccagcca gccggaaggg ccgagcgcag aagtggtcct    9180
```

```
gcaactttat ccgcctccat ccagtctatt aattgttgcc gggaagctag agtaagtagt    9240
tcgccagtta atagtttgcg caacgttgtt gccattgcta caggcatcgt ggtgtcacgc    9300
tcgtcgtttg gtatggcttc attcagctcc ggttcccaac gatcaaggcg agttacatga    9360
tcccccatgt tgtgcaaaaa agcggttagc tccttcggtc ctccgatcgt tgtcagaagt    9420
aagttggccg cagtgttatc actcatggtt atggcagcac tgcataattc tcttactgtc    9480
atgccatccg taagatgctt ttctgtgact ggtgagtact caaccaagtc attctgagaa    9540
tagtgtatgc ggcgaccgag ttgctcttgc ccggcgtcaa tacgggataa taccgcgcca    9600
catagcagaa ctttaaaagt gctcatcatt ggaaaacgtt cttcggggcg aaaactctca    9660
aggatcttac cgctgttgag atccagttcg atgtaaccca ctcgtgcacc caactgatct    9720
tcagcatctt ttactttcac cagcgtttct gggtgagcaa aaacaggaag gcaaaatgcc    9780
gcaaaaaagg gaataagggc gacacggaaa tgttgaatac tcatactctt cctttttcaa    9840
tattattgaa gcatttatca gggttattgt ctcatgagcg gatacatatt tgaatgtatt    9900
tagaaaaata aacaaatagg ggttccgcgc acatttcccc gaaaagtgc                9949
```

```
<210> SEQ ID NO 2
<211> LENGTH: 3040
<212> TYPE: DNA
<213> ORGANISM: Artificial sequence
<220> FEATURE:
<223> OTHER INFORMATION: pEn plasmid

<400> SEQUENCE: 2
```

```
gacgaaaggg cctcgtgata cgcctatttt tataggttaa tgtcatgata ataatggttt      60
cttagacgtc aggtggcact tttcggggaa atgtgcgcgg aaccccscatt tgtttatttt    120 tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga ccacgatgcc tgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca aacaaaaaaa ccaccgctac cagcggtggt ttgtttgccg gatcaagagc   1320
```

```
taccaactct tttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt   1860 gctggccttt tgctcacatg ttctttcctg cgttatcccc tgattctgtg ataaccgta   1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagttt gcacgcctgc cgttcgacga tttgataaga attccctagg   2280
actagtttac gctcatgatc gcggcatgtc ctgatatttt tcctctaaaa aagataaaaa   2340
gtcttttcgc ttcggcagaa gaggttcatc atgaacaaaa attcggcatt tttaaaaatg   2400
cctatagcta aatccggaac gacactttag aggtttctgg gtcatcctga ttcagacata   2460
gtgttttgaa tataggatcc gagctcaagc ttagatctgg tacctctaga cgcccgccat   2520
aaactgccag gcatcaaatt aagcagaagg ccatcctgac ggatggcctt tttgcgtttc   2580
tacaaactct tcctgtgcta gcctcgagaa tctctggaag atccgcgcgt accgagttct   2640
aattcactgg ccgtcgtttt acaacgtcgt gactgggaaa accctggcgt tacccaactt   2700
aatcgccttg cagcacatcc cccttttcgc cagctggcgta atagcgaaga ggcccgcacc   2760
gatcgccctt cccaacagtt gcgcagcctg aatggcgaat ggcgcctgat gcggtatttt   2820
ctccttacgc atctgtgcgg tatttcacac cgcatatggt gcactctcag tacaatctgc   2880
tctgatgccg catagttaag ccagccccga cacccgccaa cacccgctga cgcgccctga   2940
cgggcttgtc tgctcccggc atccgcttac agacaagctg tgaccgtctc cgggagctgc   3000
atgtgtcaga ggttttcacc gtcatcaccg aaacgcgcga   3040

<210> SEQ ID NO 3
<211> LENGTH: 6901
<212> TYPE: DNA
<213> ORGANISM: Artificial sequence
<220> FEATURE:
<223> OTHER INFORMATION: pEnH1 plasmid

<400> SEQUENCE: 3
gacgaaaggg cctcgtgata cgcctatttt tataggttaa tgtcatgata ataatggttt     60
cttagacgtc aggtggcact tttcggggaa atgtgcgcgg aacccccatt tgtttatttt    120
tctaaataca ttcaaatatg tatccgctca tgagacaata accctgataa atgcttcaat    180
aatattgaaa aaggaagagt atgagtattc aacatttccg tgtcgccctt attcccttt     240 ttgcggcatt ttgccttcct gttttgtctc acccagaaac gctggtgaaa gtaaagatg    300 ctgaagatca gttgggtgca cgagtgggtt acatcgaact ggatctcaac agcggtaaga    360
```

-continued

```
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200 cagacccgt agaaaagatc aaaggatctt cttgagatcc ttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca atactgttc   1380 ttctagtgta gccgtagtta ggccaccact caagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga cggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 ggggggcggag cctatggaaa aacgccagca acgcggcctt tttacggttc ctggccttt   1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagttt gcacgcctgc cgttcgacga tttgataaga attccctagg   2280
actagtttac gctcatgatc gcggcatgtc ctgatatttt tcctctaaaa aagataaaaa   2340
gtcttttcgc ttcggcagaa gaggttcatc atgaacaaaa attcggcatt tttaaaaatg   2400
cctatagcta aatccggaac gacactttag aggtttctgg tcatcctga ttcagacata   2460 gtgttttgaa tataggatcc aaggagatat accatggcga ccggcaaagg cgcggcagct   2520
tccacgcagg aaggcaagtc ccaaccattc aaggtcacgc cggggccatt cgatccagcc   2580
acatggctgg aatggtcccg ccagtggcag ggcactgaag gcaacggcca cgcggccgcg   2640
tccggcattc cggcctgga tgcgctggca ggcgtcaaga tcgcgccggc gcagctgggt   2700
gatatccagc agcgctacat gaaggacttc tcagcgctgt ggcaggccat ggccgagggc   2760
```

```
aaggccgagg ccaccggtcc gctgcacgac cggcgcttcg ccggcgacgc atggcgcacc    2820
aacctcccat atcgcttcgc tgccgcgttc tacctgctca atgcgcgcgc cttgaccgag    2880
ctggccgatg ccgtcgaggc cgatgccaag acccgccagc gcatccgctt cgcgatctcg    2940
caatgggtcg atgcgatgtc gcccgccaac ttccttgcca ccaatcccga ggcgcagcgc    3000
ctgctgatcg agtcgggcgg cgaatcgctg cgtgccggcg tgcgcaacat gatggaagac    3060
ctgacacgcg gcaagatctc gcagaccgac gagagcgcgt ttgaggtcgg ccgcaatgtc    3120
gcggtgaccg aaggcgccgt ggtcttcgag aacgagtact ccagctgtt gcagtacaag    3180 ccgctgaccg acaaggtgca cgcgcgcccg ctgctgatgg tgccgccgtg catcaacaag    3240
tactacatcc tggacctgca gccggagagc tcgctggtgc gccatgtggt ggagcaggga    3300
catacggtgt ttctggtgtc gtggcgcaat ccggacgcca gcatggccgg cagcacctgg    3360
gacgactaca tcgagcacgc ggccatccgc gccatcgaag tcgcgcgcga catcagcggc    3420
caggacaaga tcaacgtgct cggcttctgc gtgggcggca ccattgtctc gaccgcgctg    3480
gcggtgctgg ccgcgcgcgg cgagcacccg gccgccagcg tcacgctgct gaccacgctg    3540
ctggactttg ccgacacggg catcctcgac gtctttgtcg acgagggcca tgtgcagttg    3600
cgcgaggcca cgctgggcgg cggcgccggc gcgccgtgcg cgctgctgcg cggccttgag    3660
ctggccaata ccttctcgtt cttgcgcccg aacgacctgg tgtggaacta cgtggtcgac    3720
aactacctga agggcaacac gccggtgccg ttcgacctgc tgttctggaa cggcgacgcc    3780
accaacctgc cggggccgtg gtactgctgg tacctgcgcc acacctacct gcagaacgag    3840
ctcaaggtac cgggcaagct gaccgtgtgc ggcgtgccgg tggacctggc cagcatcgac    3900
gtgccgacct atatctacgg ctcgcgcgaa gaccatatcg tgccgtggac cgcggccctat   3960 gcctcgaccg cgctgctggc gaacaagctg cgcttcgtgc tgggtgcgtc gggccatatc    4020
gccggtgtga tcaacccgcc ggccaagaac aagcgcagcc actggactaa cgatgcgctg    4080
ccggagtcgc cgcagcaatg gctggccggc gccatcgagc atcacggcag ctggtggccg    4140
gactggaccg catggctggc cgggcaggcc ggcgcgaaac gcgccgcgcc cgccaactat    4200
ggcaatgcgc gctatcgcgc aatcgaaccc gcgcctgggc gatacgtcaa agccaaggca    4260
tgacgcttgc atgagtgccg gcgtgcgtca tgcacggcgc cggcaggcct gcaggttccc    4320 tcccgttcc attgaaagga ctacacaatg actgacgttg tcatcgtatc cgccgcccgc     4380
accgcggtcg gcaagtttgg cggctcgctg gccaagatcc cggcaccgga actgggtgcc    4440
gtggtcatca aggccgcgct ggagcgcgcc ggcgtcaagc cggagcaggt gagcgaagtc    4500
atcatgggcc aggtgctgac cgccggttcg ggccagaacc ccgcacgcca ggccgcgatc    4560
aaggccggcc tgccggcgat ggtgccggcc atgaccatca acaaggtgtg cggctcgggc    4620
ctgaaggccg tgatgctggc cgccaacgcg atcatggcgg gcgacgccga tcgtggtg     4680 gccggcggcc aggaaaacat gagcgccgcc ccgcacgtgc tgccgggctc gcgcgatggt    4740
ttccgcatgg gcgatgccaa gctggtcgac accatgatcg tcgacggcct gtgggacgtg    4800
tacaaccagt accacatggg catcaccgcc gagaacgtgg ccaaggaata cggcatcaca    4860
cgcgaggcgc aggatgagtt cgccgtcggc tcgcagaaca aggccgaagc cgcgcagaag    4920
gccggcaagt ttgacgaaga gatcgtcccg gtgctgatcc cgcagcgcaa gggcgacccg    4980
gtggccttca agaccgacga gttcgtgcgc cagggcgcca cgctggacag catgtccggc    5040
ctcaagcccg ccttcgacaa ggccggcacg gtgaccgcgg ccaacgcctc gggcctgaac    5100
gacggcgccg ccgcggtggt ggtgatgtcg gcggccaagg ccaaggaact gggcctgacc    5160
```

```
ccgctggcca cgatcaagag ctatgccaac gccggtgtcg atcccaaggt gatgggcatg    5220
ggcccggtgc cggcctccaa gcgcgccctg tcgcgcgccg agtggacccc gcaagacctg    5280
gacctgatgg agatcaacga ggcctttgcc gcgcaggcgc tggcggtgca ccagcagatg    5340
ggctgggaca cctccaaggt caatgtgaac ggcggcgcca tcgccatcgg ccacccgatc    5400
ggcgcgtcgg gctgccgtat cctggtgacg ctgctgcacg agatgaagcg ccgtgacgcg    5460
aagaagggcc tggcctcgct gtgcatcggc ggcggcatgg gcgtggcgct ggcagtcgag    5520
cgcaaataag gaaggggttt tccggggccg cgcgcggttg gcgcggaccc ggcgacgata    5580
acgaagccaa tcaaggagtg gacatgactc agcgcattgc gtatgtgacc ggcggcatgg    5640
gtggtatcgg aaccgccatt tgccagcggc tggccaagga tggctttcgt gtggtggccg    5700
gttgcggccc caactcgccg cgccgcgaaa agtggctgga gcagcagaag gccctgggct    5760
tcgatttcat tgcctcggaa ggcaatgtgg ctgactggga ctcgaccaag accgcattcg    5820
acaaggtcaa gtccgaggtc ggcgaggttg atgtgctgat caacaacgcc ggtatcaccc    5880
gcgacgtggt gttccgcaag atgacccgcg ccgactggga tgcggtgatc gacaccaacc    5940
tgacctcgct gttcaacgtc accaagcagg tgatcgacgg catggccgac cgtggctggg    6000
gccgcatcgt caacatctcg tcggtgaacg ggcagaaggg ccagttcggc cagaccaact    6060
actccaccgc caaggccggc ctgcatggct tcaccatggc actggcgcag gaagtggcga    6120
ccaagggcgt gaccgtcaac acggtctctc cgggctatat cgccaccgac atggtcaagg    6180
cgatccgcca ggacgtgctc gacaagatcg tcgcgacgat cccggtcaag cgcctgggcc    6240
tgccggaaga gatcgcctcg atctgcgcct ggttgtcgtc ggaggagtcc ggtttctcga    6300
ccggcgccga cttctcgctc aacgcggccg tgcatatggg ctgacctaag cttagatctg    6360
gtacctctag acgcccgcca taaactgcca ggcatcaaat taagcagaag gccatcctga    6420
cggatggcct ttttgcgttt ctacaaactc ttcctgtgct agcctcgaga atctctggaa    6480
gatccgcgcg taccgagttc taattcactg gccgtcgttt tacaacgtcg tgactgggaa    6540
aaccctggcg ttacccaact taatcgcctt gcagcacatc cccctttcgc cagctggcgt    6600
aatagcgaag aggcccgcac cgatcgccct tcccaacagt tgcgcagcct gaatggcgaa    6660
tggcgcctga tgcggtattt tctccttacg catctgtgcg gtatttcaca ccgcatatgg    6720
tgcactctca gtacaatctg ctctgatgcc gcatagttaa gccagccccg acacccgcca    6780
acacccgctg acgcgccctg acgggcttgt ctgctcccgg catccgctta cagacaagct    6840
gtgaccgtct ccgggagctg catgtgtcag aggttttcac cgtcatcacc gaaacgcgcg    6900
a                                                                    6901

<210> SEQ ID NO 4
<211> LENGTH: 4222
<212> TYPE: DNA
<213> ORGANISM: Artificial sequence
<220> FEATURE:
<223> OTHER INFORMATION: pEnRecA plasmid

<400> SEQUENCE: 4
agctcgtatt acccggcatg acaggagtaa aaatggctat cgacgaaaac aaacagaaag     60
cgttggcggc agcactgggc cagattgaga acaatttggg taaaggctcc atcatgcgcc    120
tgggtgaaga ccgttccatg gatgtggaaa ccatctctac cggttcgctt tcactggata    180
tcgcgcttgg ggcaggtggt ctgccgatgg gccgtatcgt cgaaatctac ggaccggaat    240
cttccggtaa aaccacgctg acgctgcagg tgatcgccgc agcgcagcgt gaaggtaaaa    300
```

```
cctgtgcgtt tatcgatgct gaacacgcgc tggacccaat ctacgcacgt aaactgggcg      360
tcgatatcga caacctgctg tgctcccagc cggacaccgg cgagcaggca ctggaaatct      420
gtgacgccct ggcgcgttct ggcgcagtag acgttatcgt cgttgactcc gtggcggcac      480
tgacgccgaa agcggaaatc gaaggcgaaa tcggcgactc tcacatgggc cttgcggcac      540
gtatgatgag ccaggcgatg cgtaagctgg cgggtaacct gaagcagtcc aacacgctgc      600
tgatcttcat caaccagatc cgtatgaaaa ttggtgtgat gttcggtaac ccggaaacca      660
ctaccggtgg taacgcgctg aaattctacg cctctgttcg tctcgacatc cgtcgtatcg      720
gcgcggtgaa agagggcgaa aacgtggtgg gtagcgaaac ccgcgtgaaa gtggtgaaga      780
acaaaatcgc tgcgccgttt aaacaggctg aattccagat cctctacggc gaaggtatca      840
acttctacgg cgaactggtt gacctgggcg taaaagagaa gctgatcgag aaagcaggcg      900
cgtggtacag ctacaaaggt gagaagatcg gtcagggtaa agcgaatgcg actgcctggc      960
tgaaagataa cccggaaacc gcgaaagaga tcgagaagaa agtacgtgag ttgctgctga     1020
gcaacccgaa ctcaacgccg gatttctctg tagatgatag cgaaggcgta gcagaaacta     1080
acgaagattt ttaatcgtct tgtttgatac acaagggtcg catctgcggc ccttttgctt     1140
ttttaagttg taaggatatg ccatgacaga atcaacatcc cgagctcaag cttagatctg     1200
gtacctctag acgcccgcca taaactgcca ggcatcaaat taagcagaag gccatcctga     1260
cggatggcct ttttgcgttt ctacaaactc ttcctgtgct agcctcgaga atctctggaa     1320
gatccgcgcg taccgagttc taattcactg gccgtcgttt tacaacgtcg tgactgggaa     1380
aaccctggcg ttacccaact taatcgcctt gcagcacatc ccccttcgc cagctggcgt      1440 aatagcgaag aggcccgcac cgatcgccct tcccaacagt tgcgcagcct gaatggcgaa     1500
tggcgcctga tgcggtattt tctccttacg catctgtgcg gtatttcaca ccgcatatgg     1560
tgcactctca gtacaatctg ctctgatgcc gcatagttaa gccagccccg acacccgcca     1620
acacccgctg acgcgccctg acgggcttgt ctgctcccgg catccgctta cagacaagct     1680
gtgaccgtct ccgggagctg catgtgtcag aggttttcac cgtcatcacc gaaacgcgcg     1740
agacgaaagg gcctcgtgat acgcctattt ttataggtta atgtcatgat aataatggtt     1800
tcttagacgt caggtggcac ttttcgggga atgtgcgcg gaaccccat ttgtttattt       1860 ttctaaatac attcaaatat gtatccgctc atgagacaat aaccctgata atgcttcaa      1920 taatattgaa aaaggaagag tatgagtatt caacatttcc gtgtcgccct tattccctt       1980 tttgcggcat tttgccttcc tgttttgct cacccagaaa cgctggtgaa agtaaaagat       2040
gctgaagatc agttgggtgc acgagtgggt tacatcgaac tggatctcaa cagcggtaag     2100
atccttgaga gttttcgccc cgaagaacgt tttccaatga tgagcacttt taaagttctg     2160
ctatgtggcg cggtattatc ccgtattgac gccgggcaag agcaactcgg tcgccgcata     2220
cactattctc agaatgactt ggttgagtac tcaccagtca cagaaaagca tcttacggat     2280
ggcatgacag taagagaatt atgcagtgct gccataacca tgagtgataa cactgcggcc     2340
aacttacttc tgacaacgat cggaggaccg aaggagctaa ccgctttttt gcacaacatg     2400
ggggatcatg taactcgcct tgatcgttgg gaaccggagc tgaatgaagc cataccaaac     2460
gacgagcgtg acaccacgat gcctgtagca atggcaacaa cgttgcgcaa actattaact     2520
ggcgaactac ttactctagc ttcccggcaa caattaatag actggatgga ggcggataaa     2580
gttgcaggac cacttctgcg ctcggccctt ccggctggct ggtttattgc tgataaatct     2640
ggagccggtg agcgtgggtc tcgcggtatc attgcagcac tggggccaga tggtaagccc     2700
```

-continued

```
tcccgtatcg tagttatcta cacgacgggg agtcaggcaa ctatggatga acgaaataga   2760
cagatcgctg agataggtgc ctcactgatt aagcattggt aactgtcaga ccaagtttac   2820
tcatatatac tttagattga tttaaaactt cattttaat ttaaaaggat ctaggtgaag   2880
atcctttttg ataatctcat gaccaaaatc ccttaacgtg agttttcgtt ccactgagcg   2940
tcagaccccg tagaaaagat caaaggatct tcttgagatc ctttttttct gcgcgtaatc   3000
tgctgcttgc aaacaaaaaa accaccgcta ccagcggtgg tttgtttgcc ggatcaagag   3060
ctaccaactc tttttccgaa ggtaactggc ttcagcagag cgcagatacc aaatactgtt   3120
cttctagtgt agccgtagtt aggccaccac ttcaagaact ctgtagcacc gcctacatac   3180
ctcgctctgc taatcctgtt accagtggct gctgccagtg gcgataagtc gtgtcttacc   3240
gggttggact caagacgata gttaccggat aaggcgcagc ggtcgggctg aacggggggt   3300
tcgtgcacac agcccagctt ggagcgaacg acctacaccg aactgagata cctacagcgt   3360
gagctatgag aaagcgccac gcttcccgaa gggagaaagg cggacaggta tccggtaagc   3420
ggcagggtcg gaacaggaga gcgcacgagg gagcttccag ggggaaacgc ctggtatctt   3480
tatagtcctg tcgggtttcg ccacctctga cttgagcgtc gatttttgtg atgctcgtca   3540
ggggggcgga gcctatggaa aaacgccagc aacgcggcct ttttacggtt cctggccttt   3600
tgctggcctt tgctcacat gttctttcct gcgttatccc ctgattctgt ggataaccgt   3660
attaccgcct ttgagtgagc tgataccgct cgccgcagcc gaacgaccga gcgcagcgag   3720
tcagtgagcg aggaagcgga agagcgccca atacgcaaac cgcctctccc cgcgcgttgg   3780
ccgattcatt aatgcagctg gcacgacagg tttcccgact ggaaagcggg cagtgagcgc   3840
aacgcaatta atgtgagtta gctcactcat taggcacccc aggctttaca ctttatgctt   3900
ccggctcgta tgttgtgtgg aattgtgagc ggataacaat ttcacacagg aaacagctat   3960
gaccatgatt acgccaagtt tgcacgcctg ccgttcgacg atttgataag aattccctag   4020
gactagttta cgctcatgat cgcggcatgt cctgatattt ttcctctaaa aaagataaaa   4080 agtctttttcg cttcggcaga agaggttcat catgaacaaa aattcggcat ttttaaaaat   4140
gcctatagct aaatccggaa cgacacttta gaggtttctg ggtcatcctg attcagacat   4200
agtgttttga ataggatc cg   4222
```

<210> SEQ ID NO 5
<211> LENGTH: 7833
<212> TYPE: DNA
<213> ORGANISM: Artificial sequence
<220> FEATURE:
<223> OTHER INFORMATION: pKD46EnRecA plasmid

<400> SEQUENCE: 5

```
catcgattta ttatgacaac ttgacggcta catcattcac ttttttcttca caaccggcac     60 ggaactcgct cgggctggcc ccggtgcatt ttttaaatac ccgcgagaaa tagagttgat    120
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat gcgccgcagt aacaattgct    420
caagcagatt tatcgccagc agctccgaat agcgcccttc ccttgcccg gcgttaatga    480 tttgcccaaa caggtcgctg aaatgcggct ggtgcgcttc atccggggcga aagaaccccg    540
```

```
tattggcaaa tattgacggc cagttaagcc attcatgcca gtaggcgcgc ggacgaaagt    600
aaacccactg gtgataccat tcgcgagcct ccgatgacg accgtagtga tgaatctctc    660
ctggcgggaa cagcaaaata tcacccggtc ggcaaacaaa ttctcgtccc tgattttca    720 ccaccccctg accgcgaatg gtgagattga gaatataacc tttcattccc agcggtcggt    780
cgataaaaaa atcgagataa ccgttggcct caatcggcgt taaacccgcc accagatggg    840
cattaaacga gtatcccggc agcaggggat cattttgcgc ttcagccata cttttcatac    900
tcccgccatt cagagaagaa accaattgtc catattgcat cagacattgc cgtcactgcg    960
tcttttactg gctcttctcg ctaaccaaac cggtaaccc gcttattaaa agcattctgt    1020
aacaaagcgg gaccaaagcc atgacaaaaa cgcgtaacaa aagtgtctat aatcacggca    1080
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaaatggata ttaatactga    1260
aactgagatc aagcaaaagc attcactaac cccctttcct gttttcctaa tcagcccggc    1320
atttcgcggg cgatatttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacggggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg caccggaca    2460 ttatcctgca gcgtaccggg atcgatgtga gagctgtcga acaggggat gatgcgtggc    2520 acaaattacg gctcggcgtc atcaccgctt cagaagttca caacgtgata gcaaaacccc    2580
gctccggaaa gaagtggcct gacatgaaaa tgtcctactt ccacacccctg cttgctgagg    2640 tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgtttta cctcccggga tttcatgaag ttccggctcg    2880 gtggttttcga ggccataaag tcagcttaca tggcccaggt gcagtacagc atgtgggtga    2940
```

```
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaatggac gaggcactgg ctgaaattgg ttttgtattt ggggagcaat     3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc taggactagt ttacgctcat gatcgcggca    3420
tgtcctgata ttttttcctct aaaaaagata aaaagtcttt tcgcttcggc agaagaggtt   3480
catcatgaac aaaaattcgg catttttaaa aatgcctata gctaaatccg gaacgacact    3540
ttagaggttt ctgggtcatc ctgattcaga catagtgttt tgaatatagg atccgagctc    3600
gtattacccg gcatgacagg agtaaaaatg gctatcgacg aaaacaaaca gaaagcgttg    3660
gcggcagcac tgggccagat tgagaaacaa tttggtaaag gctccatcat gcgcctgggt    3720
gaagaccgtt ccatggatgt ggaaaccatc tctaccggtt cgctttcact ggatatcgcg    3780
cttggggcag gtggtctgcc gatgggccgt atcgtcgaaa tctacggacc ggaatcttcc    3840
ggtaaaacca cgctgacgct gcaggtgatc gccgcagcgc agcgtgaagg taaaacctgt    3900
gcgtttatcg atgctgaaca cgcgctggac ccaatctacg cacgtaaact gggcgtcgat    3960
atcgacaacc tgctgtgctc ccagccggac accggcgagc aggcactgga aatctgtgac    4020
gccctggcgc gttctggcgc agtagacgtt atcgtcgttg actccgtggc ggcactgacg    4080
ccgaaagcgg aaatcgaagg cgaaatcggc gactctcaca tgggccttgc ggcacgtatg    4140
atgagccagg cgatgcgtaa gctggcgggt aacctgaagc agtccaacac gctgctgatc    4200
ttcatcaacc agatccgtat gaaaattggt gtgatgttcg gtaacccgga accactacc     4260 ggtggtaacg cgctgaaatt ctacgcctct gttcgtctcg acatccgtcg tatcggcgcg    4320
gtgaaagagg gcgaaaacgt ggtgggtagc gaaacccgcg tgaaagtggt gaagaacaaa    4380
atcgctgcgc cgtttaaaca ggctgaattc cagatcctct acggcgaagg tatcaacttc    4440
tacggcgaac tggttgacct gggcgtaaaa gagaagctga tcgagaaagc aggcgcgtgg    4500
tacagctaca aggtgagaa gatcggtcag ggtaaagcga atgcgactgc ctggctgaaa     4560
gataacccgg aaccgcgaa agagatcgag aagaaagtac gtgagttgct gctgagcaac     4620
ccgaactcaa cgccggattt ctctgtagat gatagcgaag cgtagcaga aactaacgaa     4680 gattttaat cgtcttgttt gatacacaag ggtcgcatct gcggcccttt tgcttttta      4740 agttgtaagg atatgccatg acagaatcaa catcccgagc tcaagcttag atctggtacc    4800
tctagacgcc cgccataaac tgccaggcat caaattaagc agaaggccat cctgacggat    4860
ggcctttttg cgtttctaca aactcttcct gtgcatgggt atggacagtt ttcccttga     4920 tatgtaacgg tgaacagttg ttctactttt gtttgttagt cttgatgctt cactgataga    4980
tacaagagcc ataagaacct cagatccttc cgtatttagc cagtatgttc tctagtgtgg    5040
ttcgttgttt ttgcgtgagc catgagaacg aaccattgag atcatactta ctttgcatgt    5100
cactcaaaaa ttttgcctca aaactggtga gctgaatttt tgcagttaaa gcatcgtgta    5160
gtgtttttct tagtccgtta cgtaggtagg aatctgatgt aatggttgtt ggtattttgt    5220
caccattcat ttttatctgg ttgttctcaa gttcggttac gagatccatt tgtctatcta    5280
gttcaacttg gaaaatcaac gtatcagtcg ggcggcctcg cttatcaacc accaatttca    5340
```

```
tattgctgta agtgtttaaa tctttactta ttggtttcaa aacccattgg ttaagccttt    5400
taaactcatg gtagttattt tcaagcatta acatgaactt aaattcatca aggctaatct    5460
ctatatttgc cttgtgagtt ttcttttgtg ttagttcttt taataaccac tcataaatcc    5520
tcatagagta tttgttttca aaagacttaa catgttccag attatatttt atgaattttt    5580
ttaactggaa aagataaggc aatatctctt cactaaaaac taattctaat ttttcgcttg    5640
agaacttggc atagtttgtc cactggaaaa tctcaaagcc tttaaccaaa ggattcctga    5700
tttccacagt tctcgtcatc agctctctgg ttgctttagc taatacacca taagcatttt    5760
ccctactgat gttcatcatc tgagcgtatt ggttataagt gaacgatacc gtccgttctt    5820
tccttgtagg gttttcaatc gtggggttga gtagtgccac acagcataaa attagcttgg    5880
tttcatgctc cgttaagtca tagcgactaa tcgctagttc atttgctttg aaaacaacta    5940
attcagacat acatctcaat tggtctaggt gattttaatc actataccaa ttgagatggg    6000
ctagtcaatg ataattacta gtccttttcc tttgagttgt gggtatctgt aaattctgct    6060
agacctttgc tggaaaactt gtaaattctg ctagaccctc tgtaaattcc gctagacctt    6120
tgtgtgtttt ttttgtttat attcaagtgg ttataattta tagaataaag aaagaataaa    6180 aaagataaa aagaatagat cccagccctg tgtataactc actactttag tcagttccgc    6240
agtattacaa aaggatgtcg caaacgctgt ttgctcctct acaaaacaga ccttaaaacc    6300
ctaaaggctt aagtagcacc ctcgcaagct cggttgcggc cgcaatcggg caaatcgctg    6360
aatattcctt ttgtctccga ccatcaggca cctgagtcgc tgtcttttc gtgacattca    6420 gttcgctgcg ctcacggctc tggcagtgaa tgggggtaaa tggcactaca ggcgcctttt    6480
atggattcat gcaaggaaac tacccataat acaagaaaag cccgtcacgg gcttctcagg    6540
gcgttttatg gcgggtctgc tatgtggtgc tatctgactt tttgctgttc agcagttcct    6600
gccctctgat tttccagtct gaccacttcg gattatcccg tgacaggtca ttcagactgg    6660
ctaatgcacc cagtaaggca gcggtatcat caacggggtc tgacgctcag tggaacgaaa    6720
actcacgtta agggattttg gtcatgagat tatcaaaaag gatcttcacc tagatccttt    6780
taaattaaaa atgaagtttt aaatcaatct aaagtatata tgagtaaact tggtctgaca    6840
gttaccaatg cttaatcagt gaggcaccta tctcagcgat ctgtctattt cgttcatcca    6900
tagttgcctg actccccgtc gtgtagataa ctacgatacg ggagggctta ccatctggcc    6960
ccagtgctgc aatgataccg cgagacccac gctcaccggc tccagattta tcagcaataa    7020
accagccagc cggaagggcc gagcgcagaa gtggtcctgc aactttatcc gcctccatcc    7080
agtctattaa ttgttgccgg gaagctagag taagtagttc gccagttaat agtttgcgca    7140
acgttgttgc cattgctaca ggcatcgtgg tgtcacgctc gtcgtttggt atggcttcat    7200
tcagctccgg ttcccaacga tcaaggcgag ttacatgatc ccccatgttg tgcaaaaaag    7260
cggttagctc cttcggtcct ccgatcgttg tcagaagtaa gttggccgca gtgttatcac    7320
tcatggttat ggcagcactg cataattctc ttactgtcat gccatccgta agatgctttt    7380
ctgtgactgg tgagtactca accaagtcat tctgagaata gtgtatgcgg cgaccgagtt    7440
gctcttgccc ggcgtcaata cgggataata ccgcgccaca tagcagaact ttaaaagtgc    7500
tcatcattgg aaaacgttct tcggggcgaa aactctcaag gatcttaccg ctgttgagat    7560
ccagttcgat gtaacccact cgtgcaccca actgatcttc agcatctttt actttcacca    7620
gcgtttctgg gtgagcaaaa acaggaaggc aaaatgccgc aaaaaaggga ataagggcga    7680
cacggaaatg ttgaatactc atactcttcc ttttcaata ttattgaagc atttatcagg    7740
```

| | |
|---|---:|
| gttattgtct catgagcgga tacatatttg aatgtattta gaaaaataaa caaataggg | 7800 |
| ttccgcgcac atttccccga aaagtgccac ctg | 7833 |

<210> SEQ ID NO 6
<211> LENGTH: 5586
<212> TYPE: DNA
<213> ORGANISM: Artificial sequence
<220> FEATURE:
<223> OTHER INFORMATION: pEnH5 plasmid

<400> SEQUENCE: 6

| | |
|---|---:|
| gacgaaaggg cctcgtgata cgcctatttt tataggttaa tgtcatgata ataatggttt | 60 |
| cttagacgtc aggtggcact tttcggggaa atgtgcgcgg aaccccattt gtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct tttccgaag gtaactggct tcagcagagc gcagatacca aatactgttc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga acggggggtt | 1560 |
| cgtgcacaca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg atttttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |
| ttaccgcctt tgagtgagct gataccgctc gccgcagccg aacgaccgag cgcagcgagt | 1980 |

```
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagttt gcacgcctgc cgttcgacga tttgataaga attccctagg   2280
actagtttac gctcatgatc gcggcatgtc ctgatatttt tcctctaaaa agataaaaa   2340 gtcttttcgc ttcggcagaa gaggttcatc atgaacaaaa attcggcatt tttaaaaatg   2400
cctatagcta aatccggaac gacactttag aggtttctgg gtcatcctga ttcagacata   2460
gtgttttgaa tataggatcc aaggagatat accatgagta atgaagtatc tataaaagaa   2520
ttaattgaaa aggcaaaggt ggcacaaaaa aaattggaag cctatagtca agaacaagtt   2580
gatgtactag taaaagcact aggaaaagtg gtttatgata atgcagaaat gtttgcaaaa   2640
gaagcagttg aagaaacaga aatgggtgtt tatgaagata aagtagctaa atgtcatttg   2700
aaatcaggag ctatttggaa tcatataaaa gacaagaaaa ctgtaggcat aataaaagaa   2760
gaacctgaaa gggcacttgt ttatgttgct aagccaaagg gagttgtggc agctactacg   2820
cctataacta atccagtggt aactcctatg tgtaatgcaa tggctgctat aaagggcaga   2880
aatacaataa tagtagcacc acatcctaaa gcaaagaaag tttcagctca tactgtagaa   2940
cttatgaatg ctgagcttaa aaaattggga gcaccagaaa atatcataca gatagtagaa   3000
gcaccatcaa gagaagctgc taaggaactt atggaaagtg ctgatgtagt tattgctaca   3060
ggcggtgctg aagagttaa agctgcttac tccagtggaa gaccagctta tggcgttgga   3120
cctggaaatt cacaggtaat agttgataag ggatacgatt ataacaaagc tgcacaggat   3180
ataataacag gaagaaaata tgacaatgga attatatgtt cttcagagca atcagttata   3240
gctcctgctg aagattatga taaggtaata gcagcttttg tagaaaatgg ggcattctat   3300
gtagaagatg aggaaacagt agaaaagttt agatcaactt tatttaaaga tggaaaaata   3360
aacagcaaga ttataggtaa atccgtccaa attattgcgg atcttgcagg agtaaaagta   3420
ccagaaggta ctaaggttat agtacttaag ggtaaaggtg caggagaaaa agatgtactt   3480
tgtaaagaaa aaatgtgtcc agttttagta gcattgaaat atgatacttt gaagaagca   3540 gttgaaatag ctatggctaa ttatatgtat gaaggagctg gtcatacagc aggcatacat   3600
tctgacaatg acgagaacat aagatatgca ggaactgtat tacctataag cagattagtt   3660
gtaaatcagc ctgcaactac tgctggagga agtttcaata atggatttaa ccctactact   3720
acactaggct gcggatcatg ggcagaaac agtatttcag aaaatcttac ttacgagcat   3780
cttataaatg tttcaagaat agggtatttc aataagaag caaagttcc tagctatgag   3840 gaaatatggg gataagtcct gttattaaaa agtatataag gaggaaaaaa tatgaagtta   3900
ttaaaattgg cacctgatgt ttataaattt gactactgcag aggagtttat gaaatactt   3960 aaggttggaa aaggtgactt tatacttact aatgaatttt tatataacc tttccttgag   4020 aaattcaatg atggtgcaga tgctgtattt caggagaat atggactcgg tgaaccttct   4080
gatgaaatga taaacaatat aattaaggat attggagata acaatataa tagaattatt   4140 gctgtagggg gaggatctgt aatagatata gccaaaatcc tcagtcttaa gtatactgat   4200
gattcattgg atttgtttga gggaaaagta cctcttgtaa aaacaaaga attaattata   4260 gttccaacta catgtggaac aggttcgaaa gttacaaatg tatcagttgc agaattaaag   4320
agaagacata ctaaaaaagg aattgcttca gacgaattat atgcaactta tgcagtactt   4380
```

```
gtaccagaat ttataaaagg acttccatat aagttttttg taaccagctc cgtagatgcc    4440
ttaatacatg caacagaagc ttatgtatct ccaaatgcaa atccttatac tgatatgttt    4500
agtgtaaaag ctatggagtt aattttaaat ggatacatgc aaatggtaga gaaaggaaat    4560
gattacagag ttgaaataat tgaggatttt gttataggca gcaattatgc aggtatagct    4620
tttggaaatg caggagtggg agcggttcac gcactctcat atccaatagg cggaaattat    4680
catgtgcctc atgagaagc aaattatctg tttttacag aaatattaa aacttattat        4740 gagaaaaatc caaatggcaa gattaaagat gtaaataaac tattagcagg catactaaaa    4800
tgtgatgaaa gtgaagctta tgacagttta tcacaacttt tagataaatt attgtcaaga    4860
aaaccattaa gagaatatgg aatgaaagag gaagaaattg aaacttttgc tgattcagta    4920
atagaaggac agcagagact gttggtaaac aattatgaac cttttcaag agaagacata     4980 gtaaacacat ataaaagtt atattaatat gtaacctaca atcattaaat atcccatctt     5040
aagaggtacc tctagacgcc cgccataaac tgccaggcat caaattaagc agaaggccat    5100
cctgacggat ggcctttttg cgtttctaca aactcttcct gtgctagcct cgagaatctc    5160
tggaagatcc gcgcgtaccg agttctaatt cactggccgt cgttttacaa cgtcgtgact    5220
gggaaaaccc tggcgttacc caacttaatc gccttgcagc acatcccct ttcgccagct    5280 ggcgtaatag cgaagaggcc cgcaccgatc gcccttccca cagttgcgc agcctgaatg     5340 gcgaatggcg cctgatgcgg tattttctcc ttacgcatct gtgcggtatt tcacaccgca    5400
tatggtgcac tctcagtaca atctgctctg atgccgcata gttaagccag ccccgacacc    5460
cgccaacacc cgctgacgcg ccctgacggg cttgtctgct cccggcatcc gcttacagac    5520
aagctgtgac cgtctccggg agctgcatgt gtcagaggtt ttcaccgtca tcaccgaaac    5580
gcgcga                                                               5586

<210> SEQ ID NO 7
<211> LENGTH: 7991
<212> TYPE: DNA
<213> ORGANISM: Artificial sequence
<220> FEATURE:
<223> OTHER INFORMATION: pMCSH5 plasmid

<400> SEQUENCE: 7
tcgagggggg gcccggtacc cagcttttgt tccctttagt gagggttaat tgcgcgcttg      60
gcgtaatcat ggtcatagct gtttcctgtg tgaaattgtt atccgctcac aattccacac     120
aacatacgag ccggaagcat aaagtgtaaa gcctggggtg cctaatgagt gagctaactc     180
acattaattg cgttgcgctc actgcccgct ttccagtcgg gaaacctgtc gtgccagctg     240
cattaatgaa tcggccaacg cgcggggaga ggcggtttgc gtattgggcg catgcataaa    300
aactgttgta attcattaag cattctgccg acatggaagc catcacaaac ggcatgatga    360
acctgaatcg ccagcggcat cagcaccttg tcgccttgcg tataatattt gcccatgggg    420
gtgggcgaag aactccagca tgagatcccc gcgctggagg atcatccagc cggcgtcccg    480
gaaaacgatt ccgaagccca acctttcata aaggcggcg gtggaatcga atctcgtga     540 tggcaggttg gcgtcgctt ggtcggtcat ttcgaacccc agagtcccgc tcagaagaac     600
tcgtcaagaa ggcgatagaa ggcgatgcgc tgcgaatcgg gagcggcgat accgtaaagc    660
acgaggaagc ggtcagccca ttcgccgcca agctcttcag caatatcacg ggtagccaac    720
gctatgtcct gatagcggtc cgccacaccc agccggccac agtcgatgaa tccagaaaag    780
cggccatttt ccaccatgat attcggcaag caggcatcgc catgggtcac gacgagatcc    840
```

```
tcgccgtcgg gcatgcgcgc cttgagcctg gcgaacagtt cggctggcgc gagcccctga    900
tgctcttcgt ccagatcatc ctgatcgaca agaccggctt ccatccgagt acgtgctcgc    960
tcgatgcgat gtttcgcttg gtggtcgaat gggcaggtag ccggatcaag cgtatgcagc   1020
cgccgcattg catcagccat gatggatact ttctcggcag gagcaaggtg agatgacagg   1080
agatcctgcc ccggcacttc gcccaatagc agccagtccc ttcccgcttc agtgacaacg   1140
tcgagcacag ctgcgcaagg aacgcccgtc gtggccagcc acgatagccg cgctgcctcg   1200
tcctgcagtt cattcagggc accggacagg tcggtcttga caaaaagaac cgggcgcccc   1260
tgcgctgaca gccggaacac ggcggcatca gagcagccga ttgtctgttg tgcccagtca   1320
tagccgaata gcctctccac ccaagcggcc ggagaacctg cgtgcaatcc atcttgttca   1380
atcatgcgaa acgatcctca tcctgtctct tgatcagatc ttgatcccct gcgccatcag   1440
atccttggcg gcaagaaagc catccagttt actttgcagg gcttcccaac cttaccagag   1500
ggcgccccag ctggcaattc cggttcgctt gctgtccata aaaccgccca gtctagctat   1560
cgccatgtaa gcccactgca agctacctgc tttctctttg cgcttgcgtt ttcccttgtc   1620
cagatagccc agtagctgac attcatccca ggtggcactt ttcggggaaa tgtgcgcgcc   1680
cgcgttcctg ctggcgctgg gcctgtttct ggcgctggac ttcccgctgt ccgtcagca   1740 gcttttcgcc cacggccttg atgatcgcgg cggccttggc ctgcatatcc cgattcaacg   1800
gccccagggc gtccagaacg ggcttcaggc gctcccgaag gtctcgggcc gtctcttggg   1860
cttgatcggc cttcttgcgc atctcacgcg ctcctgcggc ggcctgtagg gcaggctcat   1920 accccctgccg aaccgctttt gtcagccggt cggccacggc ttccggcgtc tcaacgcgct   1980
ttgagattcc cagcttttcg gccaatccct gcggtgcata ggcgcgtggc tcgaccgctt   2040
gcgggctgat ggtgacgtgg cccactggtg gccgctccag ggcctcgtag aacgcctgaa   2100
tgcgcgtgtg acgtgccttg ctgccctcga tgccccgttg cagccctaga tcggccacag   2160
cggccgcaaa cgtggtctgg tcgcgggtca tctgcgcttt gttgccgatg aactccttgg   2220
ccgacagcct gccgtcctgc gtcagcggca ccacgaacgc ggtcatgtgc gggctggttt   2280
cgtcacggtg gatgctggcc gtcacgatgc gatccgcccc gtacttgtcc gccagccact   2340
tgtgcgcctt ctcgaagaac gccgctgct gttcttggct ggccgacttc caccattccg   2400
ggctggccgt catgacgtac tcgaccgcca acacagcgtc cttgcgccgc ttctctggca   2460
gcaactcgcg cagtcggccc atcgcttcat cggtgctgct ggccgcccag tgctcgttct   2520
ctggcgtcct gctggcgtca gcgttgggcg tctcgcgctc gcgtaggcg tgcttgagac   2580 tggccgccac gttgcccatt tcgccagct tcttgcatcg catgatcgcg tatgccgcca   2640
tgcctgcccc tcccttttgg tgtccaaccg gctcgacggg ggcagcgcaa ggcggtgcct   2700
ccggcgggcc actcaatgct tgagtatact cactagactt tgcttcgcaa agtcgtgacc   2760
gcctacggcg gctgcggcgc cctacgggct tgctctccgg gcttcgccct gcgcggtcgc   2820
tgcgctccct tgccagcccg tggatatgtg gacgatggcc gcgagcggcc accggctggc   2880
tcgcttcgct cggcccgtgg acaaccctgc tggacaagct gatggacagg ctgcgcctgc   2940
ccacgagctt gaccacaggg attgcccacc ggctacccag ccttcgacca cataccacc    3000 ggctccaact gcgcggcctg cggccttgcc ccatcaattt tttaatttt ctctggggaa    3060 aagcctccgg cctgcggcct gcgcgcttcg cttgccggtt ggacaccaag tggaaggcgg   3120
gtcaaggctc gcgcagcgac cgcgcagcgg cttggccttg acgcgcctgg aacgacccaa   3180
gcctatgcga gtgggggcag tcgaaggcga agcccgcccg cctgcccccc gagcctcacg   3240
```

```
gcggcgagtg cggggggttcc aaggggggcag cgccaccttg ggcaaggccg aaggccgcgc   3300
agtcgatcaa caagccccgg aggggccact ttttgccgga gggggagccg cgccgaaggc   3360
gtgggggaac cccgcagggg tgcccttctt tgggcaccaa agaactagat atagggcgaa   3420
atgcgaaaga cttaaaaatc aacaacttaa aaaagggggg tacgcaacag ctcattgcgg   3480 cacccccgc aatagctcat tgcgtaggtt aaagaaaatc tgtaattgac tgccactttt   3540
acgcaacgca taattgttgt cgcgctgccg aaaagttgca gctgattgcg catggtgccg   3600
caaccgtgcg gcaccctacc gcatggagat aagcatggcc acgcagtcca gagaaatcgg   3660
cattcaagcc aagaacaagc ccggtcactg ggtgcaaacg gaacgcaaag cgcatgaggc   3720
gtgggccggg cttattgcga ggaaacccac ggcggcaatg ctgctgcatc acctcgtggc   3780
gcagatgggc caccagaacg ccgtggtggt cagccgaaag acactttcca agctcatcgg   3840
acgttctttg cggacggtcc aatacgcagt caaggacttg gtggccgagc gctggatctc   3900
cgtcgtgaag ctcaacggcc ccggcaccgt gtcggcctac gtggtcaatg accgcgtggc   3960
gtggggccag ccccgcgacc agttgcgcct gtcggtgttc agtgccgccg tggtggttga   4020
tcacgacgac caggacgaat cgctgttggg gcatggcgac ctgcgccgca tcccgaccct   4080
gtatccgggc gagcagcaac taccgaccgg ccccggcgag gagccgccca gccagcccgg   4140
cattccgggc atggaaccag acctgccagc cttgaccgaa acggaggaat gggaacggcg   4200
cgggcagcag cgcctgccga tgcccgatga gccgtgtttt ctggacgatg gcgagccgtt   4260
ggagccgccg acacgggtca cgctgccgcg ccggtagcac ttgggttgcg cagcaacccg   4320
taagtgcgct gttccagact atcggctgta gccgcctcgc cgccctatac cttgtctgcc   4380
tccccgcgtt gcgtcgcggt gcatggagcc gggccacctc gacctgaatg gaagccggcg   4440
gcacctcgct aacggattca ccgttttat caggctctgg gaggcagaat aaatgatcat   4500
atcgtcaatt attacctcca cggggagagc ctgagcaaac tggcctcagg catttgagaa   4560
gcacacggtc acactgcttc cggtagtcaa taaaccggta aaccagcaat agacataagc   4620
ggctatttaa cgaccctgcc ctgaaccgac gaccgggtcg aatttgcttt cgaatttctg   4680
ccattcatcc gcttattatc acttattcag gcgtagcacc aggcgtttaa gggcaccaat   4740
aactgcctta aaaaaattac gccccgccct gccactcatc gcagtcggcc tattggttaa   4800
aaaatgagct gatttaacaa aaatttaacg cgaattttaa caaatatta acgcttacaa   4860 tttccattcg ccattcaggc tgcgcaactg ttgggaaggg cgatcggtgc gggcctcttc   4920
gctattacgc cagctggcga aaggggggatg tgctgcaagg cgattaagtt gggtaacgcc   4980
agggttttcc cagtcacgac gttgtaaaac gacggccagt gagcgcgcgt aatacgactc   5040
actatagggc gaattggagc tccaccgcgg tggcggccgc tctagaacta gtggatcccc   5100
cgggctgcag gaattcccta ggactagttt acgctcatga tcgcggcatg tcctgatatt   5160
tttcctctaa aaagataaa aagtcttttc gcttcggcag aagaggttca tcatgaacaa   5220
aaattcggca ttttttaaaaa tgcctatagc taaatccgga acgacacttt agaggtttct   5280
gggtcatcct gattcagaca tagtgttttg aatataggat ccaaggagat ataccatgag   5340
taatgaagta tctataaaag aattaattga aaaggcaaag gtgcacaaa aaaaattgga   5400 agcctatagt caagaacaag ttgatgtact agtaaaagca ctaggaaaag tggtttatga   5460
taatgcagaa atgtttgcaa agaagcagt tgaagaaaca gaaatgggtg tttatgaaga   5520
taaagtagct aaatgtcatt tgaaatcagg agctatttgg aatcatataa agacaagaa   5580 aactgtaggc ataataaaag aagaacctga aagggcactt gtttatgttg ctaagccaaa   5640
```

```
gggagttgtg gcagctacta cgcctataac taatccagtg gtaactccta tgtgtaatgc    5700
aatggctgct ataaagggca gaaatacaat aatagtagca ccacatccta aagcaaagaa    5760
agtttcagct catactgtag aacttatgaa tgctgagctt aaaaaattgg gagcaccaga    5820
aaatatcata cagatagtag aagcaccatc aagagaagct gctaaggaac ttatggaaag    5880
tgctgatgta gttattgcta caggcggtgc tggaagagtt aaagctgctt actccagtgg    5940
aagaccagct tatggcgttg gacctggaaa ttcacaggta atagttgata agggatacga    6000
ttataacaaa gctgcacagg atataataac aggaagaaaa tatgacaatg gaattatatg    6060
ttcttcagag caatcagtta tagctcctgc tgaagattat gataaggtaa tagcagcttt    6120
tgtagaaaat ggggcattct atgtagaaga tgaggaaaca gtagaaaagt ttagatcaac    6180
tttatttaaa gatggaaaaa taaacagcaa gattataggt aaatccgtcc aaattattgc    6240
ggatcttgca ggagtaaaag taccagaagg tactaaggtt atagtactta agggtaaagg    6300
tgcaggagaa aaagatgtac tttgtaaaga aaaaatgtgt ccagttttag tagcattgaa    6360
atatgatact tttgaagaag cagttgaaat agctatggct aattatatgt atgaaggagc    6420
tggtcataca gcaggcatac attctgacaa tgacgagaac ataagatatg caggaactgt    6480
attacctata agcagattag ttgtaaatca gcctgcaact actgctggag gaagttttcaa   6540 taatggattt aaccctacta ctacactagg ctgcggatca tggggcagaa acagtatttc    6600
agaaaatctt acttacgagc atcttataaa tgtttcaaga atagggtatt tcaataaaga    6660
agcaaaagtt cctagctatg aggaaatatg gggataagtc ctgttattaa aaagtatata    6720
aggaggaaaa aatatgaagt tattaaaatt ggcacctgat gtttataaat ttgatactgc    6780
agaggagttt atgaaatact ttaaggttgg aaaaggtgac tttatactta ctaatgaatt    6840
tttatataaa cctttccttg agaaattcaa tgatggtgca gatgctgtat ttcaggagaa    6900
atatggactc ggtgaacctt ctgatgaaat gataaacaat ataattaagg atattggaga    6960
taaacaatat aatagaatta ttgctgtagg gggaggatct gtaatagata tagccaaaat    7020
cctcagtctt aagtatactg atgattcatt ggatttgttt gagggaaaag tacctcttgt    7080
aaaaaacaaa gaattaatta tagttccaac tacatgtgga acaggttcag aagttacaaa    7140
tgtatcagtt gcagaattaa agagaagaca tactaaaaaa ggaattgctt cagacgaatt    7200
atatgcaact tatgcagtac ttgtaccaga atttataaaa ggacttccat ataagttttt    7260
tgtaaccagc tccgtagatg ccttaataca tgcaacagaa gcttatgtat ctccaaatgc    7320
aaatccttat actgatatgt ttagtgtaaa agctatggag ttaattttaa atggatacat    7380
gcaaatggta gagaaaggaa atgattacag agttgaaata attgaggatt tgttataggg   7440
cagcaattat gcaggtatag cttttggaaa tgcaggagtg ggagcggttc acgcactctc    7500
atatccaata ggcggaaatt atcatgtgcc tcatggagaa gcaaattatc tgttttttac    7560
agaaatattt aaaacttatt atgagaaaaa tccaaatggc aagattaaag atgtaaataa    7620
actattagca ggcatactaa aatgtgatga agtgaagct tatgacagtt tatcacaact    7680
tttagataaa ttattgtcaa gaaaaccatt aagagaatat ggaatgaaag aggaagaaat    7740
tgaaactttt gctgattcag taatagaagg acagcagaga ctgttggtaa acaattatga    7800 accttttca agagaagaca tagtaaacac atataaaaag ttatattaat atgtaaccta    7860
caatcattaa atatcccatc ttaagaggta cctctagacg cccgccataa actgccaggc    7920
atcaaattaa gcagaaggcc atcctgacgg atggccttt tgcgtttcta caaactcttc     7980
ctgtgctagc c                                                         7991
```

```
<210> SEQ ID NO 8
<211> LENGTH: 71
<212> TYPE: DNA
<213> ORGANISM: Artificial sequence
<220> FEATURE:
<223> OTHER INFORMATION: SadF primer

<400> SEQUENCE: 8
atgaccatta ctccggcaac tcatgcaatt tcgataaatc ctgccacggg gtgtaggctg    60
gagctgcttc g                                                         71

<210> SEQ ID NO 9
<211> LENGTH: 70
<212> TYPE: DNA
<213> ORGANISM: Artificial sequence
<220> FEATURE:
<223> OTHER INFORMATION: SadR primer

<400> SEQUENCE: 9
cccgaaacgc ggtcatttct ggggtaacat tcgccagaac cgttggcgga attccgggga    60
tccgtcgacc                                                           70

<210> SEQ ID NO 10
<211> LENGTH: 71
<212> TYPE: DNA
<213> ORGANISM: Artificial sequence
<220> FEATURE:
<223> OTHER INFORMATION: GabDF primer

<400> SEQUENCE: 10
atgaaactta acgacagtaa cttattccgc cagcaggcgt tgattaacgg gtgtaggctg    60
gagctgcttc g                                                         71

<210> SEQ ID NO 11
<211> LENGTH: 70
<212> TYPE: DNA
<213> ORGANISM: Artificial sequence
<220> FEATURE:
<223> OTHER INFORMATION: GabDR primer

<400> SEQUENCE: 11
gcctttctcc agcgcatcgg caatatgctc ttccactttt gctaccgctt attccgggga    60
tccgtcgacc                                                           70

<210> SEQ ID NO 12
<211> LENGTH: 30
<212> TYPE: DNA
<213> ORGANISM: Artificial sequence
<220> FEATURE:
<223> OTHER INFORMATION: RecAF primer

<400> SEQUENCE: 12
gtgagctcgt attacccggc atgacaggag                                     30

<210> SEQ ID NO 13
<211> LENGTH: 30
<212> TYPE: DNA
<213> ORGANISM: Artificial sequence
<220> FEATURE:
<223> OTHER INFORMATION: RecAR primer

<400> SEQUENCE: 13
gtgagctcgg gatgttgatt ctgtcatggc                                     30
```

```
<210> SEQ ID NO 14
<211> LENGTH: 39
<212> TYPE: DNA
<213> ORGANISM: Artificial sequence
<220> FEATURE:
<223> OTHER INFORMATION: H1#F primer

<400> SEQUENCE: 14
ggatccaagg agatatacca tggcgaccgg caaaggcgc                              39

<210> SEQ ID NO 15
<211> LENGTH: 26
<212> TYPE: DNA
<213> ORGANISM: Artificial sequence
<220> FEATURE:
<223> OTHER INFORMATION: H1#R primer

<400> SEQUENCE: 15
aagcttaggt cagcccatat gcaggc                                           26

<210> SEQ ID NO 16
<211> LENGTH: 44
<212> TYPE: DNA
<213> ORGANISM: Artificial sequence
<220> FEATURE:
<223> OTHER INFORMATION: H5#F primer

<400> SEQUENCE: 16
ggatccaagg agatatacca tgagtaatga agtatctata aaag                       44

<210> SEQ ID NO 17
<211> LENGTH: 29
<212> TYPE: DNA
<213> ORGANISM: Artificial sequence
<220> FEATURE:
<223> OTHER INFORMATION: H5#R primer

<400> SEQUENCE: 17
agatctctct taagatggga tatttaatg                                        29
```